(12) United States Patent
Danishefsky et al.

(10) Patent No.: US 9,493,580 B2
(45) Date of Patent: Nov. 15, 2016

(54) MULTIVALENT GLYCOPEPTIDE CONSTRUCTS AND USES THEREOF

(75) Inventors: Samuel J. Danishefsky, Englewood, NJ (US); Govind Ragupathi, New York, NY (US); Philip O. Livingston, New York, NY (US); Jianglong Zhu, New York, NY (US); David R. Spriggs, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 30 days.

(21) Appl. No.: 13/703,563

(22) PCT Filed: Jun. 10, 2011

(86) PCT No.: PCT/US2011/040074
§ 371 (c)(1),
(2), (4) Date: Dec. 13, 2012

(87) PCT Pub. No.: WO2011/156774
PCT Pub. Date: Dec. 15, 2011

(65) Prior Publication Data
US 2013/0095173 A1    Apr. 18, 2013

Related U.S. Application Data

(60) Provisional application No. 61/353,722, filed on Jun. 11, 2010.

(51) Int. Cl.
*A61K 39/00* (2006.01)
*A61K 31/70* (2006.01)
*C07K 17/02* (2006.01)
*C07K 1/107* (2006.01)

(52) U.S. Cl.
CPC ........... *C07K 17/02* (2013.01); *A61K 39/0011* (2013.01); *C07K 1/1075* (2013.01); *A61K 2039/60* (2013.01); *A61K 2039/6081* (2013.01)

(58) Field of Classification Search
USPC .................. 514/23, 25, 54; 424/193.1, 194.1
See application file for complete search history.

(56) References Cited

U.S. PATENT DOCUMENTS

| | | |
|---|---|---|
| 5,977,081 A | 11/1999 | Marciani |
| 6,080,725 A | 6/2000 | Marciani |
| 6,090,789 A | 7/2000 | Danishefsky et al. |
| 6,184,344 B1 | 2/2001 | Kent et al. |
| 6,645,935 B2 | 11/2003 | Danishefsky et al. |
| 6,660,714 B1 | 12/2003 | Danishefsky et al. |
| 7,018,637 B2 | 3/2006 | Chong et al. |
| 7,160,856 B2 | 1/2007 | Danishefsky et al. |
| 7,550,146 B2 | 6/2009 | Danishefsky et al. |
| 7,824,687 B2 | 11/2010 | Danishefsky et al. |
| 7,854,934 B2 | 12/2010 | Danishefsky et al. |
| 7,879,335 B1 | 2/2011 | Danishefsky et al. |
| 8,092,780 B2 | 1/2012 | Livingston et al. |
| 2002/0006900 A1 | 1/2002 | Danishefsky et al. |
| 2002/0038017 A1 | 3/2002 | Danishefsky et al. |
| 2003/0153492 A1 | 8/2003 | Danishefsky et al. |
| 2004/0102607 A1 | 5/2004 | Danishefsky et al. |
| 2006/0229432 A1 | 10/2006 | Danishefsky et al. |
| 2006/0233747 A1 | 10/2006 | Kochendoerfer et al. |
| 2009/0060938 A1 | 3/2009 | Livingston et al. |
| 2009/0317411 A1 | 12/2009 | Wong et al. |

FOREIGN PATENT DOCUMENTS

| | | |
|---|---|---|
| DE | 19802748 A1 | 7/1999 |
| EP | 315153 A2 | 5/1989 |
| JP | 55076894 A | 10/1980 |
| JP | 11035594 | 9/1999 |
| WO | WO-96/34005 A1 | 10/1996 |
| WO | WO-98/46246 A1 | 10/1998 |
| WO | WO-98/52573 A1 | 11/1998 |
| WO | WO-99/15201 A1 | 4/1999 |
| WO | WO-99/48515 A1 | 9/1999 |
| WO | WO-99/61916 A1 | 12/1999 |
| WO | WO-01/14395 A2 | 3/2001 |
| WO | WO-2004/050711 | 6/2004 |
| WO | WO-2004/060915 A2 | 7/2004 |
| WO | WO-2005/044841 A1 | 5/2005 |
| WO | WO-2007/079448 A2 | 7/2007 |
| WO | WO-2007/146070 A2 | 12/2007 |
| WO | WO-2010/005598 A1 | 1/2010 |
| WO | WO-2010/005735 A2 | 1/2010 |
| WO | WO-2010/006343 A2 | 1/2010 |

OTHER PUBLICATIONS

Allen et al. Pursuit of optimal carbohydrate-based anticancer vaccines: preparation of a multiantigenic unimolecular glycopeptide containing the Tn, MBr1, and LewisY antigens, J. Am. Chem. Soc., 123:1890-1897 (2001).

Allen et al., A second generation synthesis of the MBr1 (Globo-H) breast tumor antigen: new application of the n-pentenyl glycoside method for achieving complex carbohydrate protein linkages, Chem. Eur. J., 6(8):1366-1375 (2000).

Armstrong et al., Intraperitoneal cisplatin and paclitaxel in ovarian cancer, N Engl J Med 354(1):34-43 (2006).

Bachman et al., Recall proliferation potential of memory CE8+ T cells and antiviral protection, Journal of Immunology, 175:4677-4685 (2005).

Bayle et al., 0-(3-Butenyl), A Stable Blocking Group Removable by Ozonolysis, Carbohydrate Research, 232: 375-380 (1992).

Bischoff et al., Cell surface modifications with trifluoromethyl dinitrophenyl-soluble protein conjugates: immunogenic role of noncovalently bound hapten, International Archives of Allergy and Applied Immunology, 75:20-26 (1984). Abstract.

Biswas et al., Construction of carbohydrate-based antitumor vaccines: synthesis of glycosyl amino acids by olefin cross-metathesis, Tetrahedron Letters, 43:6107-6110 (2002).

(Continued)

*Primary Examiner* — Yan Xiao
(74) *Attorney, Agent, or Firm* — Choate, Hall & Stewart, LLP; Brenda Herschbach Jarrell; John P. Rearick

(57) ABSTRACT

Glycopeptide conjugates comprising GM2 and/or Gb5 carbohydrate determinants, and methods of making and using such conjugates are disclosed. The immunogenicity of select glycopeptide conjugates is demonstrated.

16 Claims, 7 Drawing Sheets

(56) References Cited

OTHER PUBLICATIONS

Blackwell et al., New approaches to olefin cross-metathesis, J. Am. Chem. Soc., 122:58-71 (2000).
Bosse et al., Linear synthesis of the tumor-associated carbohydrate antigens Globo-H, SSEA-3, and Gb3, J. Org. Chem., 67:6659-6670 (2002).
Broddefalk et al., Glycopeptide Analogue of Type II Collagen Use of Acid Labile Protective Groups Preparation of a—for Carbohydrate Moieties in Solid Phase Synthesis of 0-Linked Glycopeptides, Tetrahedron Letters, 37(17): 3011-3014 (1996).
Buskas et al., Towards a Fully Synthetic Carbohydrate-Based Anticancer Vaccine: Synthesis and Immunological Evaluation of a Lipidated Glycopeptide Containing the Tumor-Associated Tn Antigen, Angew. Chem. Int. Ed., 44: 5985-5988 (2005).
Cabaret, Amphiphilic Liposaccharides. Synthesis and Reductive Cleavage of C-allyl, 0-allyl, and 0-butenyl Glycosyl Derivatives, Carbohydrate Research, 189: 341-348 (1989).
Cho et al. Organic synthesis in pursuit of immunology: large-scale synthesis of peracetylated GM2 glycosylamino acid for preparation of a multiantigenic prostate cancer vaccine, Bioorg. Med. Chem. 13(17):5259-5266 (2005).
Danishefsky et al., From the laboratory to the clinic: a retrospective on fully synthetic carbohydrate-based anticancer vaccines frequently used abbreviations are listed in the appendix, Angew. Chem. Int. Ed. Engl.39(5):836 (2000).
Danishefsky et al., Glycals in organic synthesis: The evolution of comprehensive strategies for the assembly of oligosaccharides and glycoconjugates of biological consequence, Angew. Chem. Int. Ed. Engl., 35:1380 (1996).
Database BIOSIS [Online] Biosciences Information Service, Philadelphia, PA, US; Mar. 22, 2002, Kovbasnjuk Olga et al., Glycosphingolipid Gb3 as biomarker for invasive colon carcinoma cells, FASEB Journal, 16(5):A1200 (2002). Annual Meeting of Professional Research Scientists on Experimental Biology; New Orleans, LA, USA, (2002).
Doolan et al., HLA-DR-Promiscuous T Cell Epitopes From Plasmodium falciparum Pre-Erythrocytic-Stage Antigens Restricted by Multiple HLA Class II Alleles, J. Immunol., 165: 1123-1137 (2000).
Dziadek et al., Biomimetic synthesis of the tumor-associated (2,3)-sialyl-T antigen and its incorporation into glycopeptide antigens from the mucins MUC1 and MUC4, Chem. Eur. J. 2004, 10(17):4150 (2004).
Efferson et al., Stimulation of human T cells by an influenza A vector expressing a CTL epitope from the HER-2/neu rotooncogene results in higher numbers of antigen-specific TCRhi cells than stimulation with peptide. divergent roles of IL-2 and IL-15, Anticancer Research, 25:715-724 (2005).
Eggermont et al., EORTC 18961: Post-operative adjuvant Ganglioside GM2-KLH21 Vaccination Treatment vs Observation in Stage II (T3-T4N0M0) Melanoma: 2nd Interim Analysis Led to an Early Disclosure of the Results, Journal of Clinical Oncology, 26(15S): 9004 (2008).
Eggermont et al., Randomized phase III trial comparing postoperative adjuvant ganglioside GM2-KLH/QS-21 vaccination versus observation in stage II (T3-T4N0M0 melanoma: final results of study EORTC 18961, J Clin. Onc., 28(15):8505 (Supplement) (2010).
Eggermont et al., Utility of adjuvant systemic therapy in melanoma, Annals of Oncology 20 (Supplement 6): vi30-vi34, (2009).
Farkas-Himsley et al. The bacterial colicin active against tumor cells in vitro and in vivo is Verotoxin I., Proc. Natl. Acad. Sci. USA, 92:6996-7000 (1995).
Federici et al., Selection of carbohydrate antigens in human epithelial ovarian cancers as targets for immunotherapy: serous and mucinous tumors exhibit distinctive patterns of expression, Int J Cancer 81:193-8 (1999).
Ferezou et al., Intralipid 10%: physicochemical characterization, Nutrition, 11:930-933 (2001).
Fraser-Reid et al., N-pentenyl glycosides in organic chemistry: A contemporary example of serendipity, Synlett, 927-942 (1992).

Garg et al., Developments in the synthesis of glycopeptides containing glycosyl L-asparagine, L-serine, and L-threonine, Advances in Carbohydrate Chemistry and Biochemistry, 50: 277-310 (1994).
Gatza et al., Tumor cell lysate-pulsed dendritic cells are more effective than TCR Id protein vaccines for active immunotherapy of T cell lymphoma, Journal of Immunology, 169:5227-5235 (2002).
Gilewski et al., Immunization of metastatic breast cancer patients with a fully synthetic globo H conjugate: A phase I trial PNAS, 98:3270-3275 (2001).
Grazi et al., Abstract. Biochemical and Biophysical Research Communications, 2:121-125 (1960).
Greene et al., Protecting Groups in Organic Synthesis, 3rd Ed., John Wiley & Sons (1999).
Hardy et al., Separation of positional isomers of oligosaccharides and glycopeptides by high-performance anion-exchange chromatography with pulsed amperometric detection, Proc. Natl. Acad. Sci. USA, 85:3289 (1988).
Hashimoto et al., Armed-disarmed glycosidation strategy based on glycosyl donors and acceptors carrying phospharcamidate as a leaving group: A convergent synthesis of iobotriaosylceramide, Tetrahedral Letters, 38(52):8969-8972 (1997).
Helling et al., GM2-KLH conjugate vaccine: increased immunogenicity in melanoma patients after administration with immunological adjuvant QS-211, Cancer Res 55:2783-8 (1995).
Hermans et al., NKT cells enhance CD4+ and CD8+ T cell responses to soluble antigen in vivo through direct interaction with dendritic cells, J. Immunol. 2003, 171(10):5140 (2003).
Ingale et al., Robust Immune Responses Elicited by a Fully Synthetic Three-Component Vavccine, Nat. Chem. Biol., 3(10): 663-667 (2007).
International Search Report for PCT/US2000/022894 mailed Apr. 10, 2001.
International Search Report for PCT/US2003/022657 mailed Dec. 10, 2003.
International Search Report for PCT/US2004/040253 mailed Oct. 18, 2005.
International Search Report for PCT/US2011/040074 mailed Feb. 14, 2012.
International Search Report of PCT/US2009/050434, 6 pages (mailed Feb. 24, 2010).
Israel et al., Phase II clinical trial of GM2-KLH/QS-21 (GMK) vaccine in patients with malignant melanoma (meeting abstract), Am. Soc. of Clin. Oncology, 1-2 (1997).
Kedar et al., Cancer Immunotherapy: are the results discouraging? Can they be improved?, Advances in Cancer Research, 59:245-323 (1992).
Keding et al. Hydroxynorleucine as a glycosyl acceptor is an efficient means for introducing amino acid functionality into complex carbohydrates, Tetrahedron Lett 44:3413-16 (2003).
Keding et al., Prospects for total synthesis: A vision for a totally synthetic vaccine targeting epithelial tumors, Proc. Natl. Acad. Sci. USA., 101(33):11937 (2004).
Keding et al., Synthesis of non-natural glycosylamino acids containing tumor-associated carbohydrate antigens, Tetrahedron 59:7023-31 (2003).
Keding et al., Synthetic Carbohydrate-Based Vaccines, Carbohydrate-Based Drug Discovery 1:381 (2003).
Kim et al., Effect of immunological adjuvant combinations on the antibody and T-cell response to vaccination with MUC1-KLH and GD3-KLH conjugates, Vaccine, 19:530-537 (2001).
Ko et al., Clinical Studies of Vaccines Targeting Breast Cancer, Clinical Cancer Research, 9: 3222-3234 (2003).
Kudryashov et al., Toward optimized carbohydrate-based anticancer vaccines: Epitope clustering, carrier structure, and adjuvant all influence antibody responses to lewie conjugates in mice, Proc. Natl. Acad. Sci. USA, 98:3264-3269 (2001).
Kuduk et al., Synthetic and immunological studies on clustered modes of mucin-related Tn and TF O-linked antigens: the preparation of a glycopeptide-based vaccine for clinical trials against prostate, J. Am. Chem. Soc., 120:12474 (1998).
Kunz et al., Synthetic glycopeptides for the construction of anticancer vaccines, ACS Symposium Series, 989:293 (2008).

(56) References Cited

OTHER PUBLICATIONS

Lassaletta et al., Glycosyl imidates, Synthesis of the hexasaccharide moiety of globo H (human breast cancer) antigen, Liebigs Ann. (9):1417-1423 (1996).
Livingston et al., Carbohydrate vaccines that induce antibodies against cancer, Cancer Immunol Immunother 45:1-9 (1997).
Livingston et al., Improved survival in Stage III Melanoma patients with GM2 antibodies: a randomized trial of adjuvant vaccination with GM2 ganglioside, J. Clin. Oncol., 12:1036 (1994).
Livingston et al., Vaccines containing purified GM2 ganglioside elicit GM2 antibodies in melanoma patients, Proc. Natl. Acad. Sci. USA, 84(9), 2911 (1987).
Lloyd et al., High Performance Anion Exchange Chromatography of Reduced Oligosaccharides from Sialomucins, Glycoconjugate J., 8:493-498 (1991).
Marcaurelle et al., Recent Advances in the Chemical Synthesis of Mucin-like Glycoproteins, Glycobiology, 12(6): 69R-77R (2002).
Marciani et al., Development of semisynthetic triterpenoid saponin derivatives with immune stimulating activity, Vaccine, 18(27):3141 (2000).
Markman et al., Duration of response to second-line, platinum-based chemotherapy for ovarian cancer: implications for patient management and clinical trial design, J Clin Oncol 22(15):3120-5 (2004).
Nagorny et al., On the Emerging Role of Chemistry in the Fashioning of Biologics: Synthesis of a Bidomainal Fucosyl GM1-Based Vaccine for the Treatment of Small Cell Lung Cancer, J. Org. Chem., 74: 5157-5162 (2009).
Nicolaou et al., A practical and enantioselective synthesis of glycosphingolipids and related compounds. Total synthesis of globotriasosylceramide (Gb3), J. Am. Chem. Soc., 110:7910-7912 (1988).
Orlandi et al., Antibody and CD8+ T cell responses against HER2/neu required for tumor eradication after DNA immunization with a Flt-3 ligand fusion vaccine, Clinical Cancer Research, 13:6195-6203 (2007).
Park et al., A Total Synthesis of a Stage Specific Pentasaccharide Embryogenesis Marker, Tet. Lett., 36(50): 9089-9092 (1995).
Park et al., Total synthesis and proof of structure of a human breast tumor (Globo-H) antigen, J. Am. Chem. Soc., 118(46):11488-11500 (1996).
Phase II Clinical Trials-(PDQ), Phase II randomized study of immunological adjuvant OPT-821 with versus without polyvalent antigen-KLH conjugate vaccine in patients with ovarian epithelial, fallopian tube, or peritoneal cancer in second or third complete clinical remission, National Cancer Institute, 1-9 (2009).
Prakash et al., Glycotyping of Prostate Specific Antigen, Glycobiology, 10(2): 173-176 (2000).
Ragupathi et al., A fully synthetic globo H carbohydrate vaccine induces a focused humoral response in prostate cancer patients: a proof of principle, Angewandte Chemie. International Edition, 38(4):563-566 (1999).
Ragupathi et al., A Novel and Efficient Method for Synthetic Carbohydrate Conjugate Vaccine Preparation: Synthesis of Sialyl Tn-KLH Conjugate Using a 4-(4-N-maleimidomethyl) cyclohexane-1-carboxyl hydrazide (MMCCH) Linker arm, Glycoconjuggate Journal, 15: 217-221 (1998).
Ragupathi et al., A Preclinical Study Comparing Approaches for Augmenting the Immunogenicity of a Heptavalent KLH-Conjugate Vaccine Against Epithelial Cancers, Cancer lummonol. Immunother., 52: 608-616 (2003).
Ragupathi et al., Antibody Inducing Polyvalent Cancer Vaccines, Cancer Treat. Res., 123: 157-180 (2005).
Ragupathi et al., Comparison of antibody titers after immunization with monovalent or tetravalent KLH conjugate vaccines, Vaccine, 20(7-8):1030 (2002).
Ragupathi et al., Immunization of Mice with a Fully Synthetic Globo H Antigen Results in Antibodies against Human Cancer Cells: A Combined Chemical-Immunological Approach to the Fashioning of an Anticancer Vaccine, Angew. Chem., Int. Ed. Engl. (1997), 36(1/2), 125-128 (1997).
Ragupathi et al., On the power of chemical synthesis: Immunological evaluation of models multiantigenic carbohydrate-based cancer vaccines, Proc. Natl. Acad. Sci. USA, 99(21):13699-13704 (2002).
Ragupathi et al., Preparation and evaluation of unimolecular pentavalent and hexavalent antigenic constructs targeting prostate and breast cancer:? a synthetic route to anticancer vaccine candidates, J. Am. Chem. Soc., 128(8):2715 (2006).
Reichel et al., Synthetic Carbohydrate-Based Vaccines: Synthesis of an L-Glycero-D-Manno-Heptose Antigen-T-Epitope-Lipopeptide Conjugate, Chem. Commun., 2087-2088 (1997).
Sabbatini et al., Consolidation for ovarian cancer in remission, J Clin Oncol 24(4):537-9 (2006).
Sabbatini et al., Immunization of ovarian cancer patients with a synthetic lewisy-protein conjugate vaccine: a phase 1 trial, Int. J. Cancer., 87:79 (2000).
Sabbatini et al., Pilot study of a heptavalent vaccine-keyhole limpet hemocyanin conjugate plus QS21 in patients with epithelial ovarian, fallopian tube, or peritoneal cancer, Clin Ca Res 13(14):4170-7 (2007).
Saul et al., End of the Road for Yet Another Melanoma Vaccine, European Journal of Cancer, 44(16): 2333-2337 (2008).
Schmidt et al., New aspects of glycoside bond formation, Pure Appl. Chem., 71(5):729 (1999).
Schmitt et al., Synthesis and Characterization of Chelator-Lipids for Reversible Immobilization of Engineered Proteins at Self-Assembled Lipid Interfaces, J. Am. Chem. Soc., 116: 8485-8491 (1994).
Severin et al., Pentose phosphate synthesis in cardiac muscle and the role of erythrose-4-phosphate in the process Abstract, Biokhimiya (Moscow), 38:583-588 (1973).
Sierra et al., Dead Ends and Detours En Route to Total Syntheses of the 1990s A list of abbreviations can be found at the end of the article, Agnew Chem. Int. Ed. Engl., 39:1538-1559 (2000).
Slovin et al., A Bivalent Conjugate Vaccine in the Treatment of Biochemically Relapsed Prostate Cancer: A Study of Glycosylated MUC-2-KLH and Globo H-KLH Conjugate Vaccines Given With the New Semi-Synthetic Saponin Immunological Adjuvant GPI-0100 or QS-21, Vaccine, 23: 3114-3122 (2005).
Slovin et al., Carbohydrate Vaccines as Immunotherapy for Cancer, Immunol. Cell Biol., 83: 418-428 (2005).
Slovin et al., Carbohydrate Vaccines in Cancer: Immunogenicity of a Fully Synthetic Globo H Hexasaccharide Conjugate in Man, Prov. Natl. Acad. Sci., 96(10): 5710-5715 (1999).
Slovin et al., Fully synthetic carbohydrate-based vaccines in biochemically relapsed prostate cancer: clinical trial results with α-N-acetylgalactosamine-O-serine/threonine conjugate vaccine, J Clin Oncol 21:4292-8 (2003).
Slovin et al., Thomsen-Friedenreich (TF) Antigen as a Target for Prostate Cancer Vaccine: Clinical Trial Results with TF Cluster (c)-KLH plus QS21 Conjugate Vaccine in Patients with Biochemically Relapsed Prostate Cancer, Cancer Immunol Immunother 54(7):694-702 (2005).
Toyokuni et al., Synthetic carbohydrate vaccines based on tumour-associated antigens, Chem. Soc. Rev., 24:231-242 (1995).
Toyokuni et al., Synthetic Carbohydrate Vaccines: Synthesis and Immunogenicity of Tn Antigen Conjugates, Bioorg. Med. Chem., 2:1119-1132 (1994).
Udodong et al., A Ready, Convergent Synthesis of the Heptasaccharide GPI Membrane Anchor of Rat Brain Thy-1 Glycoprotein., J. Am. Chem. Soc., 115: 7886-7887 (1993).
Wan et al.,Olefin cross-metathesis: a powerful tool for constructing vaccines composed of multimeric antigens, J Carbohydrate Chem, 24:425-440 (2005).
Warren et al., Synthetic glycopeptide-based vaccines, Topics in Current Chemistry, 267:109-141 (2007).
Westerlind et al., Synthetic vaccines consisting of tumor-associated muc1 glycopeptide antigens and a t-cell epitope for the induction of a highly specific humoral immune response, Angew. Chem., Int. Ed., 47(39) 7551 (2008).

(56) References Cited

OTHER PUBLICATIONS

Williams et al., In pursuit of an anticancer vaccine: a monomolecular construct containing multiple carbohydrate antigens, Tetrahedron Letters, 41(49): 9505-9508 (2000).

Wittrock et al., Synthetic vaccines of tumor-associated glycopeptide antigens by immune-compatible thioether linkage to bovine serum albumin, Angew. Chem. Int. Ed., 46(27):5226-5230 (2007).

Written Opinion for PCT/US2011/040074, 7 pages (Feb. 14, 2012).

Zhang et al., Augmenting the Immunogenicity of Synthetic MUC1 Peptide Vaccines in Mice, Cancer Res., 56: 3315-3319 (1996).

Zhang et al., Selection of tumor antigens as targets for immune attack using immunohistochemistry: I. focus on gangliosides, Int J Cancer 73:42-49 (1997).

Zhang et al., Selection of tumor antigens as targets for immune attack using immunohistochemistry: II. Blood group-related antigens, Int J Cancer 73:50-56 (1997).

Zhang et al., Selection of Tumor Antigens as Targets for Immune Attack Using Immunohistochemistry: Protein Antigens 1,2, Clin. Cancer Res., 4: 2669-2676 (1998).

Zhu et al., Biologics Through Chemistry: Total Synthesis of a Proposed Dual-Acting Vaccine Targeting Ovarian Cancer by Orchestration of Oligosaccharide and Polypeptide Domains, J. Am. Chem. Soc., 131: 4151-4158 (2009).

Zhu et al., From synthesis to biologics: preclinical data on a chemistry derived anticancer vaccine, J. Am. Chem. Soc. 131(26):9298-9303 (2009).

Chang, W. et al., Expression of Globo H and SSEA3 in breast cancer stem cells and the involvement of fucosyl transferases 1 and 2 in Globo H synthesis, Proc Natl Acad Sci U S A., 105(33):11667-11672 (2008); erratum in Proc Natl Acad Sci U S A., 105(44):17206 (2008).

Attarwala, H., TGN1412: From Discovery to Disaster, Journal of Young Pharmacists, 2(3):332-336 (2010).

Check, Erica, Nerve inflammation halts trial for Alzheimer's drug, Nature, 415:462 (2002).

Lee, D. et al., 'Biologic' level structures through chemistry: a total synthesis of a unimolecular pentavalent MUCI glycopeptide construct, Tetrahedron Letters, 50:2167-2170 (2009).

U.S. Dept. of Health and Human Services, Food and Drug Administration, Guidance for Industry, Investigators, and Reviewers, Exploratory IND Studies, Pharmacology/Toxicology, 16 pages (2006).

Schenk, D. et al., Immunization with amyloid-β attenuates Alzheimer-disease-like pathology in the PDAPP mouse, Nature, 400:173-177 (1999).

1. Et$_2$NH, DMF
2. Ac$_2$O, pyridine
   78%, 2 steps
3. CF$_3$CO$_2$H, CH$_2$Cl$_2$
4. pyridine 76%, 2 steps See Figure 4C

MULTIVALENT GLYCOPEPTIDE CONSTRUCTS AND USES THEREOF

CROSS REFERENCE TO RELATED APPLICATIONS

This application is a U.S. national phase application under 35 U.S.C. §371 of international PCT application No. PCT/US2011/040074, filed Jun. 10, 2011, which claims priority to U.S. provisional patent application Ser. No. 61/353,722, filed Jun. 11 2010, the entirety of each of which is hereby incorporated herein by reference.

GOVERNMENT SUPPORT

The invention was made with United States Government support under grants CA28824 and PO1CA052477 awarded by the National Institutes of Health. The United States Government has certain rights in the invention.

BACKGROUND OF THE INVENTION

It is well-known that malignantly transformed cells often display aberrant levels and types of surface glycosylation, a feature which serves to characteristically differentiate tumor cells from normal, healthy cells. This abnormal glycosylation pattern on the tumor cell surface provides a potential opportunity for tumor immunologists to develop carbohydrate-based anticancer vaccines for cancer therapeutic treatment. Proper exposure of vaccine constructs containing tumor-associated carbohydrate antigens to the immune system would stimulate the formation of corresponding antibodies. These antibodies, in turn, would selectively bind and help eradicate tumor cells overexpressing those carbohydrate epitopes.

Toward this end, synthetic chemists and cancer immunologists have been striving to develop effective carbohydrate-based anticancer vaccines for cancer immunotherapy. In recent years, important advances in this field have been reported by others (Ingale, S.; Wolfert, M. A.; Gaekwad, J.; Buskas, T.; Boons, G.-J. *Nat. Chem. Biol.* 2007, 3, 663; Buskas, T.; Ingale, S.; Boons, G.-J. *Angew. Chem., Int. Ed.* 2005, 44, 5985; Kunz, H.; Dziadek, S.; Wittrock, S.; Becker, T. *ACS Symposium Series* 2008, 989 (*Carbohydrate-Based Vaccines*), 293; Westerlind, U.; Hobel, A.; Gaidzik, N.; Schmitt, E.; Kunz, H. *Angew. Chem., Int. Ed.* 2008, 47, 7551; Wittrock, S.; Becker, T.; Kunz, H. *Angew. Chem., Int. Ed.* 2007, 46, 5226-5230; Dziadek, S.; Brocke, C.; Kunz, H. *Chem. Eur. J.* 2004, 10, 4150; Hermans, I. F.; Silk, J. D.; Gileadi, U.; Salio, M.; Mathew, B.; Ritter, G.; Schmidt, R.; Harris, Adrian L.; Old, L.; Cerundolo, V. *J. Immunol.* 2003, 171, 5140; Schmidt, R. R.; Castro-Palomino, J. C.; Retz, O. *Pure Appl. Chem.* 1999, 71, 729), as well as by Applicant (Danishefsky, S. J.; Bilodeau, M. T. *Angew. Chem. Int. Ed. Engl.* 1996, 35, 1380; Danishefsky, S. J.; Allen, J. R. *Angew. Chem. Int. Ed. Engl.* 2000, 39, 836; Keding, S. J.; Danishefsky, S. J. *Carbohydrate-Based Drug Discovery* 2003, 1, 381; Warren, J. D.; Geng, X.; Danishefsky, S. J. *Top. Curr. Chem.* 2007, 267, 109).

Although several synthetic constructs have been developed in recent years, as described above, and in other references described herein, there remains a need for the further investigation to develop novel constructs capable of eliciting a more sustained or effective (and preferably selective) immune response. Clearly, in an effort to achieve this goal, it would be useful to develop new compositions and methods for inducing an immunogenic response as well as improved and/or novel methods for the treatment of cancer.

DEFINITIONS

Figure 1:
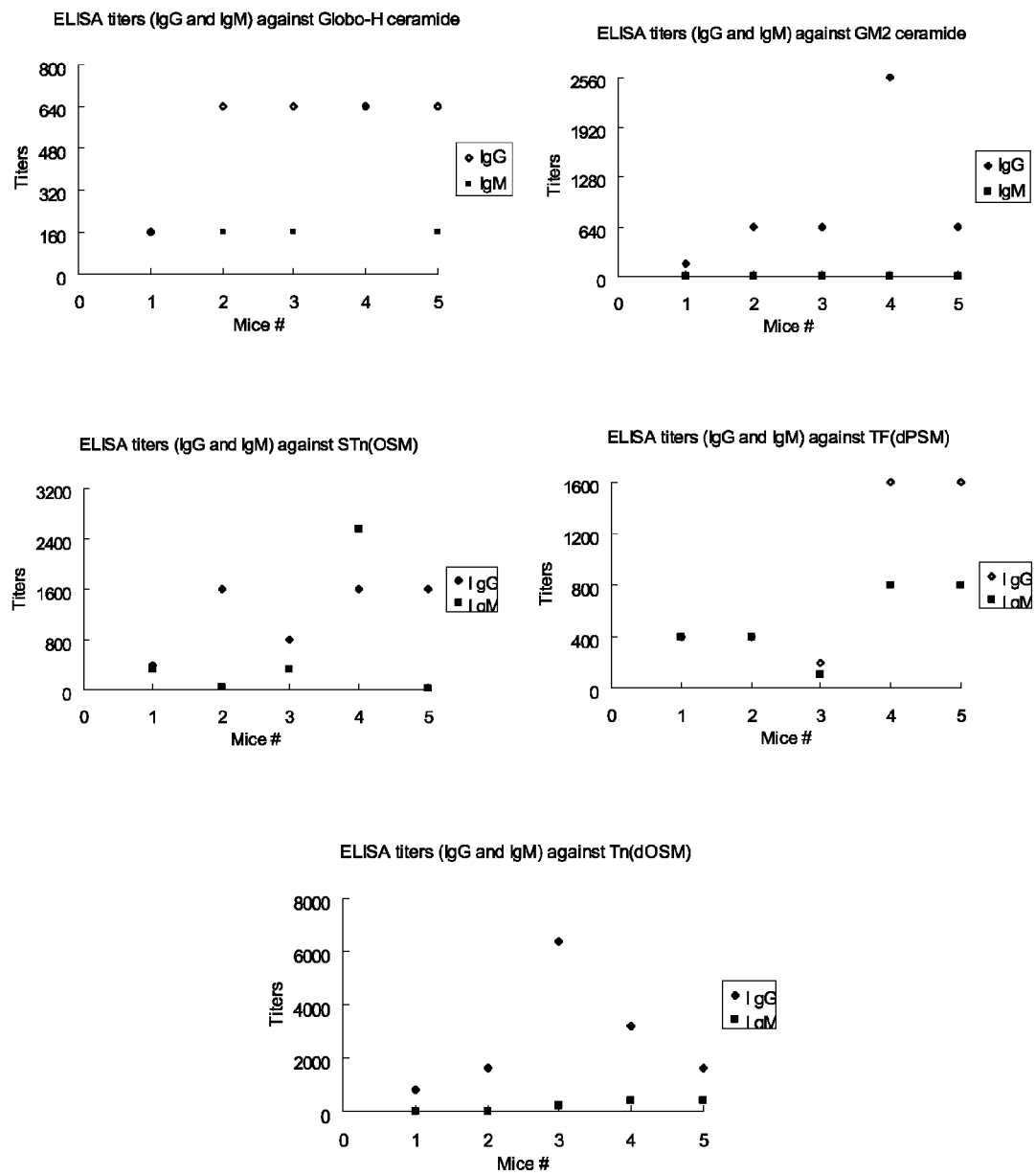
FIG. 1 depicts ELISA titer data from mice immunized with pentavalent-KLH construct 2 shown in Example 1. Mice produced substantial titers of antibodies corresponding all of the carbohydrate antigens including Globo-H ceramide, GM2 ceramide, STn (OSM), TF (dPSM) and Tn (dOSM).
Figure 2:
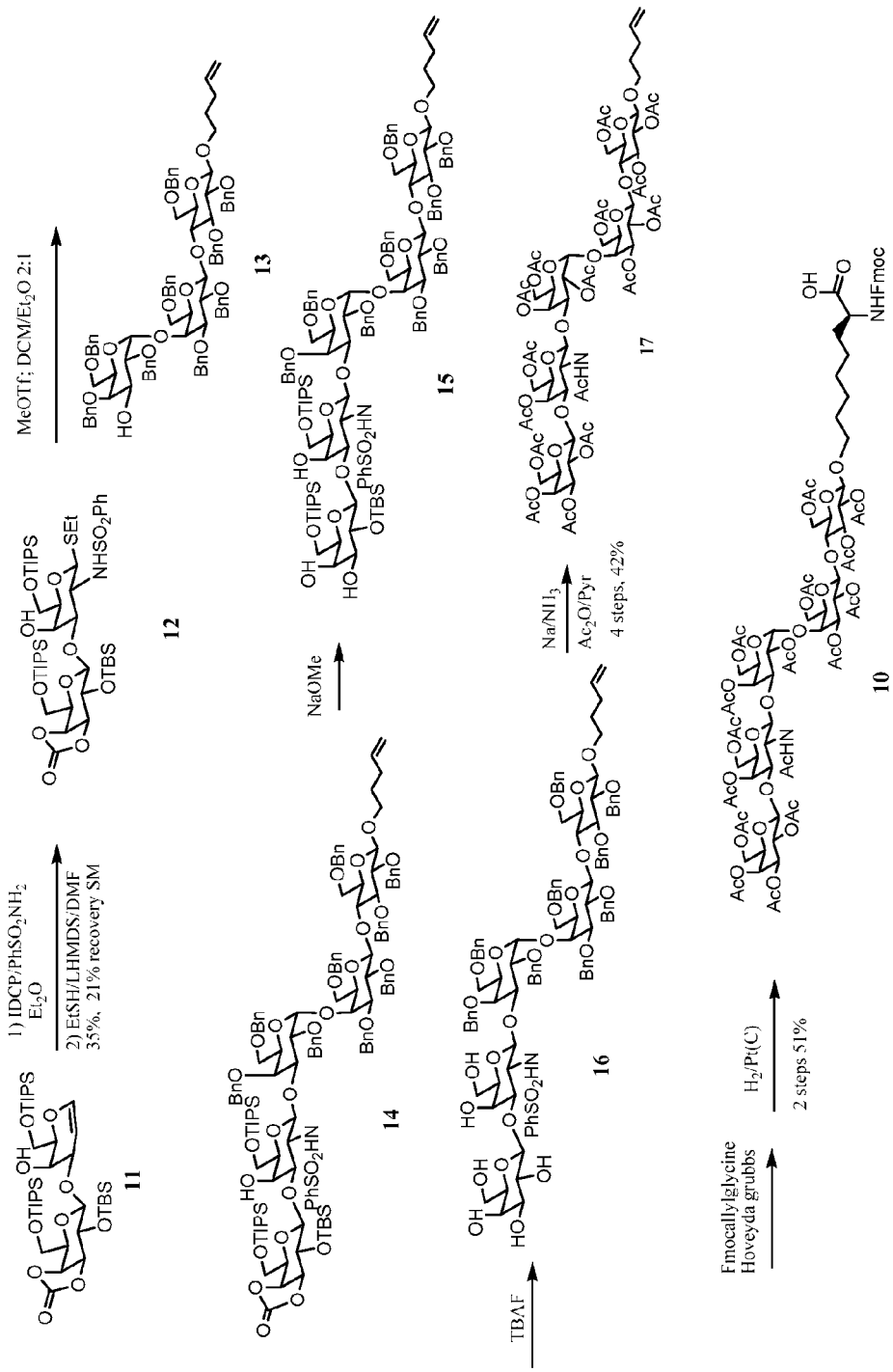
FIG. 2 depicts a synthetic scheme for the synthesis of a Gb5 glycoamino acid.

Certain compounds of the present disclosure, and definitions of specific functional groups are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

As used herein, the following definitions shall apply unless otherwise indicated.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-12 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent saturated or unsaturated, straight or branched, hydrocarbon chain," refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group. A substituted alkynylene chain is a polymethylene group containing at least one double bond in which one or more hydrogen atoms are replaced with a substituent. Suitable substituents include those described below for a substituted aliphatic group.

The term "acyl," used alone or a part of a larger moiety, refers to groups formed by removing a hydroxy group from a carboxylic acid.

The term "halogen" means F, Cl, Br, or I.

The terms "aralkyl" and "arylalkyl" are used interchangably and refer to alkyl groups in which a hydrogen atom has been replaced with an aryl group. Such groups include, without limitation, benzyl, cinnamyl, and dihyrocinnamyl.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The terms "heteroaralkyl" and "heteroarylalkyl" refer to an alkyl group substituted by a heteroaryl moiety, wherein the alkyl and heteroaryl portions independently are optionally substituted.

The term "heteroaliphatic," as used herein, means aliphatic groups wherein one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "hetercyclyl," "heterocycloaliphatic," or "heterocyclic" groups.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

In another aspect, the present disclosure provides "pharmaceutically acceptable" compositions, which comprise a therapeutically effective amount of one or more of the compounds described herein, formulated together with one or more pharmaceutically acceptable carriers (additives) and/or diluents. As described in detail, the pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Unless otherwise stated, structures depicted herein are also meant to include all isomeric (e.g., enantiomeric, diastereomeric, and geometric (or conformational)) forms of the structure; for example, the R and S configurations for each stereocenter, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure.

Provided compounds may comprise one or more saccharide moieties. Unless otherwise specified, both D- and L-configurations, and mixtures thereof, are within the scope of the disclosure. Unless otherwise specified, both α- and β-linked embodiments, and mixtures thereof, are contemplated by the present disclosure.

If, for instance, a particular enantiomer of a compound of the present disclosure is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$- enriched carbon are within the scope of this disclosure. Such compounds are useful, for example, as analytical tools, as probes in biological assays, or as therapeutic agents in accordance with the present disclosure.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. In preferred embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate(mesylate), benzylsulfonate, and tosylate (Ts).

For protecting 1,2- or 1,3-diols, the protecting groups include methylene acetal, ethylidene acetal, 1-t-butylethylidene ketal, 1-phenylethylidene ketal, (4-methoxyphenyl) ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzyl sulfonamide, trifluoromethylsulfonamide, and phenacylsulfonamide. Exemplary protecting groups are detailed herein, however, it will be appreciated that the present disclosure is not intended to be limited to these protecting groups; rather, a variety of additional equivalent protecting groups can be readily identified using the above criteria and utilized in the method of the present disclosure. Additionally, a variety of protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}R^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched)alkylene)O$-N(R^\circ)_2$; or $-(C_{1-4}$ straight or branched alkylene)C(O)O$-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6-membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)C(O)OR$^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

When used as a chemical bond, "〰" shall be understood to depict a single carbon-carbon bond with undefined stereochemistry at a carbon center. Thus, a substituent attached to a carbon atom with a "〰" bond refers to embodiments where the substituent is coming out of the plane of the paper, embodiments where the substituent is going behind the plane of the paper, and combinations (i.e., stereochemical mixtures) thereof.

The term "biomolecule", as used herein, refers to molecules (e.g., proteins, amino acids, peptides, polynucleotides, nucleotides, carbohydrates, sugars, lipids, nucleoproteins, glycopeptides, glycoproteins, lipoproteins, steroids, etc.) which belong to classes of chemical compounds, whether naturally-occurring or artificially created (e.g., by synthetic or recombinant methods), that are commonly found in cells and tissues. Examplary types of biomolecules include, but are not limited to, glycopeptides, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

The term "carbohydrate" refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula C$_n$H$_{2n}$O$_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose. (e.g., 2'-fluororibose, deoxyribose, and hexose). Carbohydrates may exist in many different forms, for example, conformers, cyclic forms, acyclic forms, stereoisomers, tautomers, anomers, and isomers.

The term "natural amino acid side chain" as used herein refers to the side chain group of any one of the common, naturally occurring L-amino acids found in naturally occurring proteins: glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met).

The term "unnatural amino acid side chain" as used herein refers to a side chain group of all amino acids which are not natural amino acids. Such amino acids include the D-isomer of any of the 20 naturally occurring amino acids Unnatural amino acids also include homoserine, ornithine, norleucine, and thyroxine. Additional unnatural amino acids are well known to one of ordinary skill in the art and include unnatural aliphatic side chains. In certain embodiments, unnatural amino acids are N-alkylated, cyclized, phosphorylated, acetylated, amidated, azidylated, labelled, and the like. In some embodiments, an unnatural amino acid is a D-isomer. In some embodiments, an unnatural amino acid is a L-isomer. In certain embodiments, an unnatural amino acid is an alpha amino acid. In other embodiments, an unnatural amino acid is a beta amino acid.

More generally, the term "amino acid", as used herein, encompasses natural amino acids and unnatural amino acids.

As used herein and in the claims, the singular forms "a", "an", and "the" include the plural reference unless the context clearly indicates otherwise. Thus, for example, a reference to "a compound" includes a plurality of such compounds.

The terms "compound," "conjugate," and "construct" are used interchangably in the present disclosure. Thus, a construct or conjugate as described herein is considered a compound, and vice versa.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "palliative" refers to treatment that is focused on the relief of symptoms of a disease and/or side effects of a therapeutic regimen, but is not curative.

As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

The expression "unit dose" as used herein refers to a physically discrete unit of a formulation appropriate for a subject to be treated. It will be understood, however, that the total daily usage of a formulation of the present invention will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts. A particular unit dose may or may not contain a therapeutically effective amount of a therapeutic agent.

An individual who is "suffering from" a disease, disorder, and/or condition has been diagnosed with and/or displays one or more symptoms of the disease, disorder, and/or condition.

An individual who is "susceptible to" a disease, disorder, and/or condition has not been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Detailed Description of Certain Embodiments

The present invention encompasses the recognition that there remains a need for glycoconjugate vaccines that are useful for the treatment of cancer and/or effective at inducing antibodies against all individual carbohydrate antigens present on the glycoconjugate.

The present invention provides, among other things, new and/or improved technologies for linking glycopeptides to carriers to generate glycoconjugates. Provided technologies permit unexpectedly large numbers of glycopeptides to be conjugated to a single carrier. In some embodiments, more than 300, 350, 400, 350, 500, 550, 600, 650, 700, 750, 800, 850, 900, 950, or 1000 glycopeptides can be conjugated to a particular carrier in accordance with the present invention.

The present invention also provides, among other things, novel technologies for providing and/or coupling glycans for use in glycopeptides and/or glycoconjugates as described herein. For example, the present invention provides technologies for the preparation and/or coupling of GM2 and/or Gb5 glycans.

The present invention further provides surprising evidence that, notwithstanding prior evidence that vaccine compositions comprising a GM2 antigen could worsen rather than improve a subject's clinical prospects, vaccine compositions comprising GM2 in the context of inventive glycopeptides and/or glycoconjugates can show significant biological benefit in model systems. The present invention therefore provides methods of treating individuals suffering from or susceptible to certain cancers by administering a vaccine composition comprising a GM2 glycan (e.g., in the context of a glycopeptide and/or glycoconjugate).

The present invention provides a variety of antigen, glycopeptide, glycoconjugate, and vaccine compositions, as well as various methods and reagents related to their preparation, identification, characterization, and/or use.

Those of ordinary skill in the art will appreciate that the present inventors have extensive experience relating to carbohydrate antigens, glycopeptide and/or glycoconjugate preparations, and their production and use. The present application describes, among other things, methods and reagents relating to the preparation, identification, characterization, and/or use of certain carbohydrate-antigen-containing compositions (e.g., glycopeptides, glycoconjugates; etc). In some embodiments, provided materials and/or methods are useful in medicine. In some embodiments, provided materials and/or methods are useful in the treatment of cancer. In some embodiments, provided materials and/or methods are useful in the treatment of solid tumors. In some embodiments, provided materials and/or methods are useful in the treatment of tumors of epithelial origin. In some embodiments, provided materials and/or methods are useful in the treatment of breast cancer, ovarian cancer, melanoma, and prostate cancer.

In a first-generation construct, which was conjugated to a KLH carrier protein, five different prostate and breast cancer associated carbohydrate antigens—Globo-H, Le$^y$, STn, TF and Tn—were incorporated on a single peptide backbone (Keding, S. J.; Danishefsky, S. J. *Proc. Natl. Acad. Sci. USA.* 2004, 101, 11937; Ragupathi, G.; Koide, F.; Livingston, P. O.; Cho, Y. S.; Atsushi, E.; Wan, Q.; Spassova, M. K.; Keding, S. J.; Allen, J.; Ouerfelli, O.; Wilson, R. M.; Danishefsky, S. J. *J. Am. Chem. Soc.* 2006, 128, 2715). This KLH conjugate was then evaluated in mice in conjunction with a suitable adjuvant (QS-21) and its immunogenicity was compared with that of the corresponding pooled monovalent vaccines. Experimental results indicated that this KLH conjugate was optimal for inducing antibodies against all of the carbohydrate antigens, with the exception of Le$^y$. The disappointing immunogenicity observed with the Le$^y$ antigen most likely arises from the fact that it is endogenously expressed at a relatively high level.

Fluorescent Activated Cell Sorter (FACS) assay analysis indicated that the antibodies induced by this first-generation unimolecular pentavalent vaccine reacted significantly with the three cell lines evaluated, which each express high levels of two or more of the corresponding antigens. These cumulative data thus suggest that the immunological properties of the individual antigens are preserved in the context of these highly elaborate vaccines.

The synthesis of a pentavalent glycopeptide construct through the assembly of a pool of glycosylamino acids presenting the Globo-H, GM2, STn, TF and Tn carbohydrate antigens (see 4-8 in Scheme 1, below), was described previously (Ragupathi, G.; Koide, F.; Livingston, P. O.; Cho, Y. S.; Atsushi, E.; Wan, Q.; Spassova, M. K.; Keding, S. J.; Allen, J.; Ouerfelli, O.; Wilson, R. M.; Danishefsky, S. J. *J. Am. Chem. Soc.* 2006, 128, 2715). In this particular construct, the previously used pentasaccharide Le$^y$ antigen was replaced with the prostate and breast cancer-associated tetrasaccharide antigen GM2. The GM2 antigen was selected for inclusion on the basis of reports which indicate that GM2-induced antibodies are active against human GM2-positive cells. Moreover, human clinical trials conducted with GM2 alone have suggested a correlation between enhanced GM2 antibody levels and survival (Livingston, P. O.; Natoli, E. J.; Calves, M. J.; Stockert, E.; Oettgen, H. F.; Old, L. *J. Proc. Natl. Acad. Sci. USA* 1987, 84, 2911; Livingston P. O.; Wong, G. Y.; Adluri, S.; Tao, Y.; Padavan, M.; Parente, R.; Hanlon, C.; Calves, M. J.; Helling, F.; Ritter, G. *J. Clin. Oncol.* 1994, 12, 1036). However, prior to the present disclosure, the immunogenicity of this pentavalent construct was not known.

The present application specifically describes, among other things, the synthesis and use superior second-generation unimolecular pentavalent constructs, useful in medicine, for example in the treatment of solid tumors such as ovarian, prostate, and/or breast cancer.

Clinical studies of cancer vaccines comprising GM2 have had limited success and are currently a controversial topic in the field of oncology. A large phase III trial, EORTC 18961, for a melanoma vaccine was halted early after an interim analysis raised serious questions regarding the safety and/or efficacy of the treatment (Eggermont, A. M. M. et al., *Annals of Oncology* 20 (Supplement 6): vi30-vi34, 2009; Saul, H., European Journal of Cancer, Issue 16, 2008). Specifically, the analysis revealed that patients receiving the treatment were less likely to survive compared with observation. For the primary endpoint, relapse free survival, the trial was deemed to have no absolutely no effect (i.e., the number of events in the observation group was exactly the same as the vaccine group).

Another melanoma trial, ECOG 1694, compared high does interferon (HDI) with a GM2-based vaccine. Interim analysis determined that HDI treatment worked better and the vaccine was seen as having no effect. Subsequent analysis suggests that this conclusion is even less negative than deserved and that the vaccine treatment is actually less effective than observation (Saul, supra).

While not wishing to be bound by any particular theory, Applicant proposes the possibility that these previous cancer vaccines containing GM2 have been unsuccessful due to their activation of sublytic levels of cell surface complement. The present invention therefore provides, in some embodiments, the identification of the previously unknown source of a problem. It is well-known in immunology that activation of the compliment cascade above a certain threshold can result in osmotic lysis of the target cell. However, incomplete, or sublytic, activation of compliment may be cell-protective (i.e., promotion of angiogenesis, proliferation, etc.) Because GM2 is not highly expressed on melanoma cells, it is possible that the GM2 vaccines used in the melanoma studies described above activated such sublytic levels of cell surface complement. Other theories have also been proposed (Saul, supra).

Regardless, prior to the teachings described herein, those of ordinary skill in the art understood that vaccines containing GM2 antigens may present unique safety and/or efficacy challenges or other defects. Against this backdrop, the present disclosure presents surprising evidence of the usefulness and effectiveness of GM-2 containing compositions as described herein in the treatment of cancer (e.g., breast cancer and other cancers such as melanoma, prostate, and ovarian cancers).

Applicant has found that a pentavalent conjugate comprising Globo-H, GM2, STn, TF, and Tn antigens induces IgG and IgM antibodies against each of the five carbohydrate antigens. Furthermore, the antibodies produced were able to react with cancer cell lines expressing these carbohydrate antigens.

The present invention encompasses the recognition that another carbohydrate antigen, Gb5, can be used in to prepare a multiantigenic immunogenic glycoconjugate (Park, T. K. et al., Tet. Lett. Vol. 36, No. 50, 9089-9092, 1995; International Patent Application Publication WO2010/005598; US Patent Application Publication 2009/0317411). In some embodiments, the present invention provides glycopeptides and/or glycoconjugates comprising Gb5 as a carbohydrate determinant.

In some embodiments, the present invention provides glycopeptides having the structure:

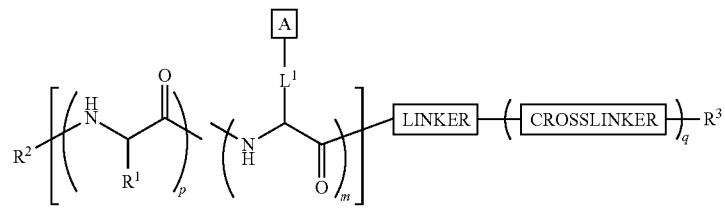

wherein
each A is independently a carbohydrate determinant found on tumor cells, wherein at least one occurrence of A is Gb5;
each $L^1$ is independently a substituted or unsubstituted aliphatic or heteroaliphatic moiety;
each $R^1$ is independently a natural or unnatural amino acid side chain;
$R^2$ is hydrogen or an amino protecting group;
$R^3$ hydrogen or an immunogenic carrier;
the crosslinker is a moiety derived from a bifunctional crosslinking reagent capable of conjugating a reactive moiety on the linker with a reactive moiety on the immunogenic carrier;
the linker is a covalent bond, an oligoester fragment comprising from 2 to about 20 hydroxy acyl residues, a peptidic fragment comprising from 2 to about 20 amino acyl residues, a linear or branched chain alkyl or aryl carboxylic ester, or an optionally substituted, bivalent $C_{1-20}$ saturated or unsaturated, straight or branched, hydrocarbon chain, wherein one to six methylene units of the chain are independently replaced by —Cy-, —$CR_2$—, —NR—, —N(R)C(O)—, —C(O)N(R)—, —N(R)$SO_2$—, —$SO_2$N(R)—, —O—, —C(O)—, —OC(O)—, —C(O)O—, —S—, —SO—, —$SO_2$—, —C(=S)—, —C(=NR)—, —N=N—, or —C(=$N_2$)—;
Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
each R is independently hydrogen or an optionally substituted group selected from $C_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, or a 5-6 membered heteroaryl ring having 1-3 heteroatoms independently selected from nitrogen, oxygen, or sulfur;
m is from 3-20;
p is from 0-100; and
q is 0 or 1.

It will be appreciated by one of ordinary skill in the art that the moiety:

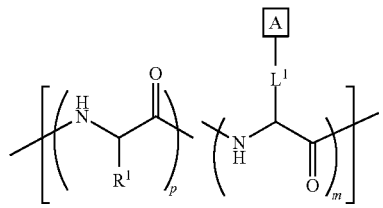

is depicted in formulae herein such that the occurrence of p-bracketed units and m-bracketed units may occur in any combination or order within the square brackets. For example, units may be arranged . . . p-m-p-m-p-m . . . , . . . p-p-m-p-m-m-p . . . , . . . m-m-m-p-p-p . . . , etc.

In some embodiments, m is from 5-20. In some embodiments, m is from 4-10. In some embodiments, m is from 5-7. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16. In some embodiments, m is 17. In some embodiments, m is 18. In some embodiments, m is 19. In some embodiments, m is 20.

In some embodiments, p is 0. In some embodiments, p is 1-100. In some embodiments, p is 1-80. In some embodiments, p is 1-50. In some embodiments, p is 1-40. In some embodiments, p is 1-30. In some embodiments, p is 1-25. In some embodiments, p is 0-20. In some embodiments, p is 0-50. In some embodiments, p is 1-20. In some embodiments, one or more occurrences of p is between occurrences of m.

In certain embodiments, q is 0. In certain embodiments, q is 0, $R^3$ is hydrogen, and the linker is a covalent bond. In other embodiments, q is 1.

In certain embodiments, one occurrence of A is Gb5 and the other occurrences of A are each independently a carbohydrate determinant found on tumor cells. In some embodiments, each occurrence of A is Gb5. In some embodiments, each A is independently a carbohydrate determinant selected from the group consisting of fucosyl GM1, $Le^x$, Gb3, KH-1, N3, globo-H, glycophorin, Tn, TF, STN, (2,3)ST, 2,6-STn, $Le^y$, GM2, and Gb5. In some embodiments, each A is independently a carbohydrate determinant selected from the group consisting of Gb5, Globo-II, STN, Tn, and TF. In some embodiments, each occurrence of A is different.

In some embodiments, each $R^1$ is independently a natural amino acid side chain. In some embodiments, each $R^1$ is independently an unnatural amino acid side chain.

In some embodiments, $R^2$ is —Ac. In other embodiments, $R^2$ is hydrogen.

In some embodiments, $R^3$ is hydrogen. In some embodiments, $R^3$ is an immunogenic carrier. In some embodiments, $R^3$ is an immunogenic carrier protein selected from human serum albumin, bovine serum albumin, cationized bovine serum albumin, polylysine, OMPC, or KLH. In some embodiments, an immunogenic carrier protein is KLH. In certain embodiments, an immunogenic carrier is a lipid having the structure:

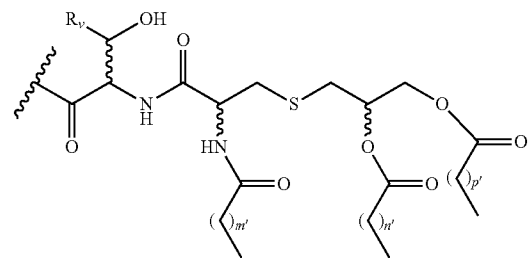

wherein m', n' and p' are each independently integers between about 8 and 20; and $R_V$ is hydrogen, substituted or unsubstituted linear or branched chain lower alkyl or substituted or unsubstituted phenyl. In certain exemplary embodiments, m', n' and p' are each 14 and the lipid is tripalmitoyl-S-glycerylcysteinylserine (e.g., PamCys).

In some embodiments, each $L^1$ is independently a branched aliphatic or heteroaliphatic moiety. In some embodiments, $L^1$ comprises a natural or unnatural amino acid side chain. In some embodiments, each occurrence of $L^1$ is independently —$CH_2(CH_2)_nO$— to provide an amino acid having the structure:

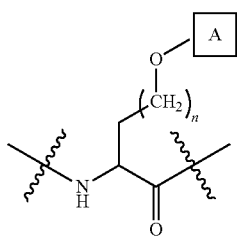

wherein n is 1-8. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8.

In some embodiments, $L^1$ is other than —O—(CHMe)- or —O—CH$_2$—.

In certain embodiments, a provided glycopeptide has the structure:

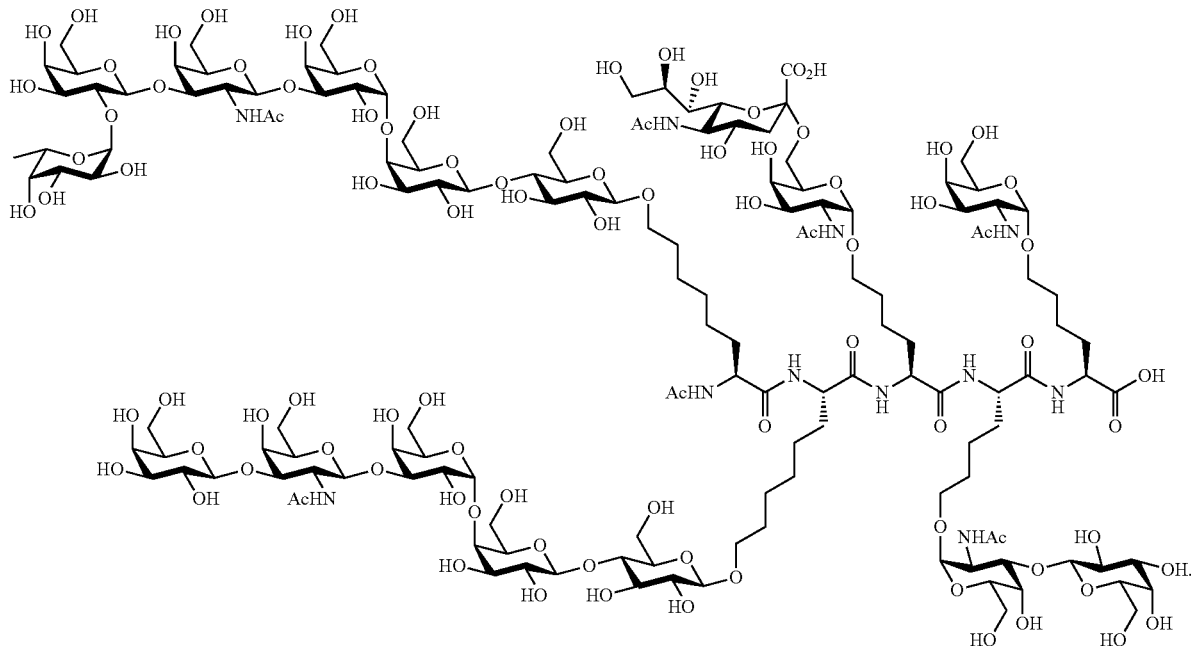

In some embodiments, a provided glycoconjugate has the structure:

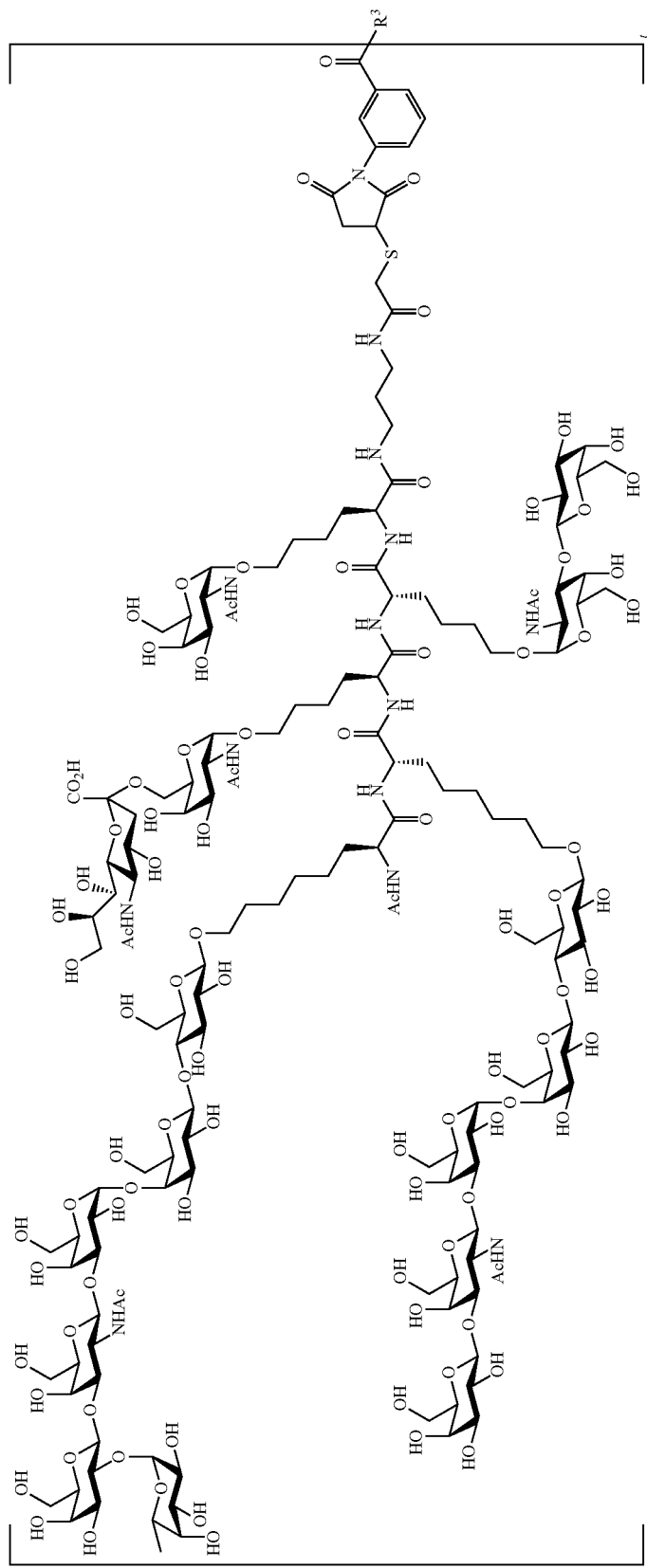

wherein R³ is an immunogenic carrier and t is the number of glycopeptide groups attached to the immunogenic carrier. In certain embodiments, t is 1. In some embodiments, t is 200-1200. In some embodiments, t is at least 200, and least 300, and least 400, at least 500, at least 600, at least 700, at least 800, at least 900, at least 1000, or at least 1100. In some embodiments, an immunogenic carrier is KLH.

Methods of Using Conjugates

In certain embodiments, the present invention provides methods of treating cancer in a subject suffering therefrom comprising administering to the subject a therapeutically effective amount of an immunogenic glycoconjugate, wherein the immunogenic glycoconjugate comprises a multi-antigenic glycopeptide having a peptidic backbone made up of at least three amino acid residues, wherein three or more of said amino acids are independently:

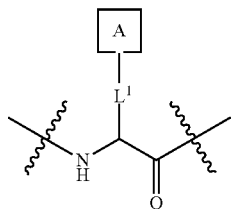

wherein each $L^1$ is independently as defined above and described in classes and subclasses herein; and each A is independently a carbohydrate determinant selected from the group consisting of Globo-H, STN, Tn, TF, Gb5, and GM2;

wherein at least one occurrence of A is Gb5 or GM2.

In certain embodiments, the glycopeptide has three occurrences of A. In some embodiments, the glycopeptide has four occurrences of A.

In some embodiments, the present invention provides methods of treating cancer in a subject suffering therefrom comprising administering to the subject a therapeutically effective amount of an immunogenic glycoconjugate, wherein the immunogenic glycoconjugate comprises a multi-antigenic glycopeptide having a peptidic backbone made up of at least five amino acid residues, wherein five or more of said amino acids are independently:

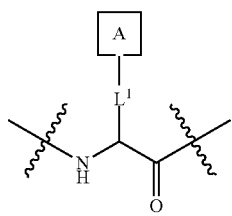

wherein each $L^1$ is independently as defined above and described in classes and subclasses herein; and each A is independently a carbohydrate determinant selected from the group consisting of Globo-H, STN, Tn, TF, Gb5, and GM2;

wherein at least one occurrence of A is Gb5 or GM2.

In some embodiments, the glycopeptide has five to seven occurrences of A. In some embodiments, the glycopeptide has five occurrences of A. In some embodiments, the glycopeptide has six occurrences of A. In some embodiments, the glycopeptide has seven occurrences of A. In some embodiments, the glycopeptide has eight occurrences of A. In some embodiments, the glycopeptide has nine occurrences of A. In some embodiments, the glycopeptide has ten occurrences of A. In some embodiments, the glycopeptide has more than ten occurrences of A.

In some embodiments, each occurrence of A is different. In other embodiments, each occurrence of A is the same.

In some embodiments, at least one occurrence of A is GM2. In some embodiments, at least once occurrence of A is Gb5. In certain embodiments, one occurrence of A is Gb5 and the other occurrences of A are each independently a carbohydrate determinant found on tumor cells. In certain embodiments, one occurrence of A is GM2 and the other occurrences of A are each independently a carbohydrate determinant found on tumor cells. In some embodiments, at least one occurrence of A is GM2 and each remaining A is independently a carbohydrate determinant selected from the group consisting of fucosyl GM1, GM2, Le$^x$, Gb3, KH-1, N3, globo-H, glycophorin, Tn, TF, STN, (2,3)ST, 2,6-STn, Le$^y$, and Gb5. In some embodiments, at least one occurrence of A is Gb5 and each remaining A is independently a carbohydrate determinant selected from the group consisting of fucosyl GM1, GM2, Le$^x$, Gb3, KH-1, N3, globo-H, glycophorin, Tn, TF, STN, (2,3)ST, 2,6-STn, Le$^y$, and Gb5.

In certain embodiments, there are five occurrences of A, wherein one occurrence of A is Gb5 and the other occurrences of A are each independently a carbohydrate determinant found on tumor cells. In certain embodiments, there are five occurrences of A, wherein one occurrence of A is GM2 and the other occurrences of A are each independently a carbohydrate determinant found on tumor cells.

In some embodiments, each A is independently a carbohydrate determinant selected from the group consisting of fucosyl GM1, GM2, Le$^x$, Gb3, KH-1, N3, globo-H, glycophorin, Tn, TF, STN, (2,3)ST, 2,6-STn, Le$^y$, and Gb5.

In some embodiments, each A is independently a carbohydrate determinant selected from the group consisting of GM2, Gb5, Globo-H, STN, Tn, and TF. In some embodiments, there are five occurrences of A, wherein each A is independently a carbohydrate determinant selected from the group consisting of Gb5, Globo-H, STN, Tn, and TF. In some embodiments, there are five occurrences of A, wherein each A is independently a carbohydrate determinant selected from the group consisting of GM2, Globo-H, STN, Tn, and TF.

In some embodiments, each $L^1$ is independently a branched aliphatic or heteroaliphatic moiety. In some embodiments, $L^1$ comprises a natural or unnatural amino acid side chain. In some embodiments, each occurrence of $L^1$ is independently —CH$_2$(CH$_2$)$_n$O— to provide an amino acid having the structure:

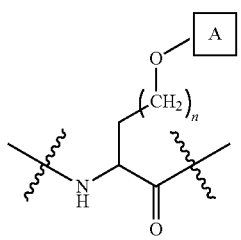

wherein n is 1-8. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8.

In some embodiments, $L^1$ is other than —O—(CHMe)- or —O—CH$_2$—.

In certain embodiments, the therapeutically effective amount of an immunogenic glycoconjugate described herein comprises an amount effective to inhibit tumor growth. In certain embodiments, the therapeutically effective amount comprises an amount effective to induce an immune response that induces a higher relative amount of IgG isotype antibodies as compared to IgM isotype antibodies. In some embodiments, the therapeutically effective amount comprises an amount effective to elicit antibodies that recognize at least one of the carbohydrate determinants. In certain embodiments, the therapeutically effective amount comprises an amount effective to elicit antibodies to each of the carbohydrate antigens. In some embodiments, the therapeutically effective amount is an amount effective to treat one or more solid tumors.

In certain embodiments, the immunogenic glycoconjugate comprises a multi-antigenic glycopeptide covalently bonded to an immunogenic carrier.

In some embodiments, the glycoconjugate has the structure:

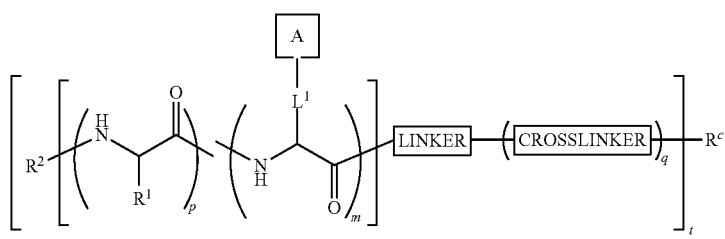

wherein each of $R^1$, $R^2$, $L^1$, A, p, m, q, t, the linker, and crosslinker is as defined above and in classes and subclases herein, and wherein $R^c$ is an immunogenic carrier.

In some embodiments, m is from 5-20. In some embodiments, m is from 4-10. In some embodiments, m is from 5-7. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16. In some embodiments, m is 17. In some embodiments, m is 18. In some embodiments, m is 19. In some embodiments, m is 20.

In some embodiments, p is 0. In some embodiments, p is 1-20. In some embodiments, one or more occurrences of p is between occurrences of m.

In certain embodiments, q is 0. In other embodiments, q is 1.

In certain embodiments, t is 1. In some embodiments, t is 200-1200. In some embodiments, t is at least 200, and least 300, and least 400, at least 500, at least 600, at least 700, at least 800, at least 900, at least 1000, or at least 1100. In some embodiments, t is from 50 to 1200. In some embodiments, t is from 200 to 800. In some embodiments, t is from 500 to 800.

In certain embodiments, the glycoconjugate has the structure:

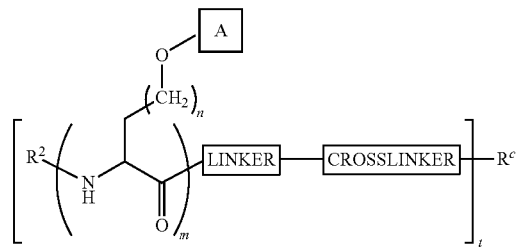

wherein each of $R^2$, m, n, t, and $R^c$ is as defined above and described in classes and subclasses herein.

In some embodiments, m is 5 and each occurrence of n is 3 or 5. In some embodiments, m is 5, each occurrence of n is 3 or 5, and each A is a carbohydrate determinant selected from the group consisting of Globo-H, STN, Tn, TF, and GM2, and wherein each occurrence of A is different. In some embodiments, m is 5, each occurrence of n is 3 or 5, and each A is a carbohydrate determinant selected from the group consisting of Globo-H, STN, Tn, TF, and Gb5, and wherein each occurrence of A is different.

In certain embodiments, the glycoconjugate has the structure:

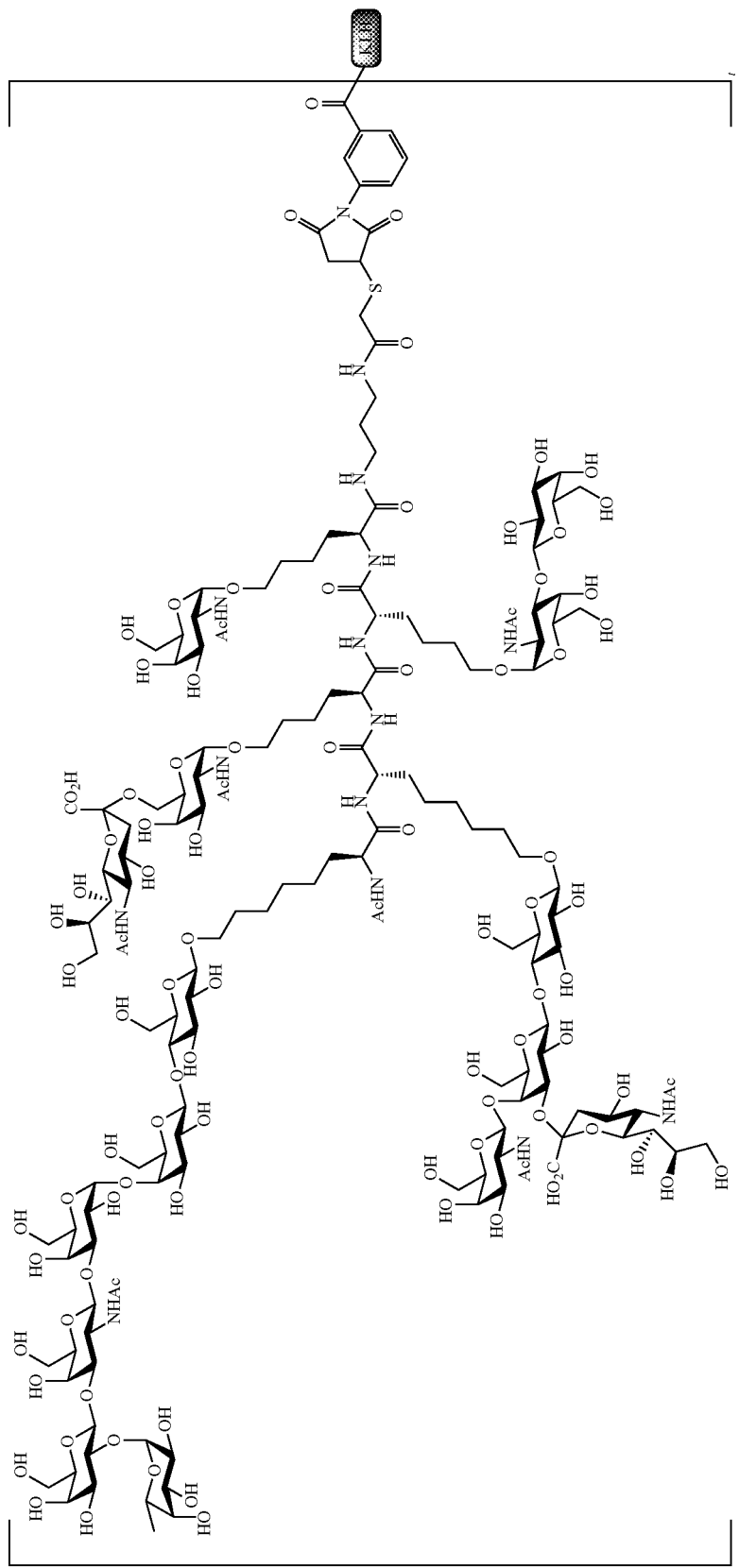

wherein t is as defined above and described in classes and subclasses herein.

In certain embodiments, the glycoconjugate has the structure:

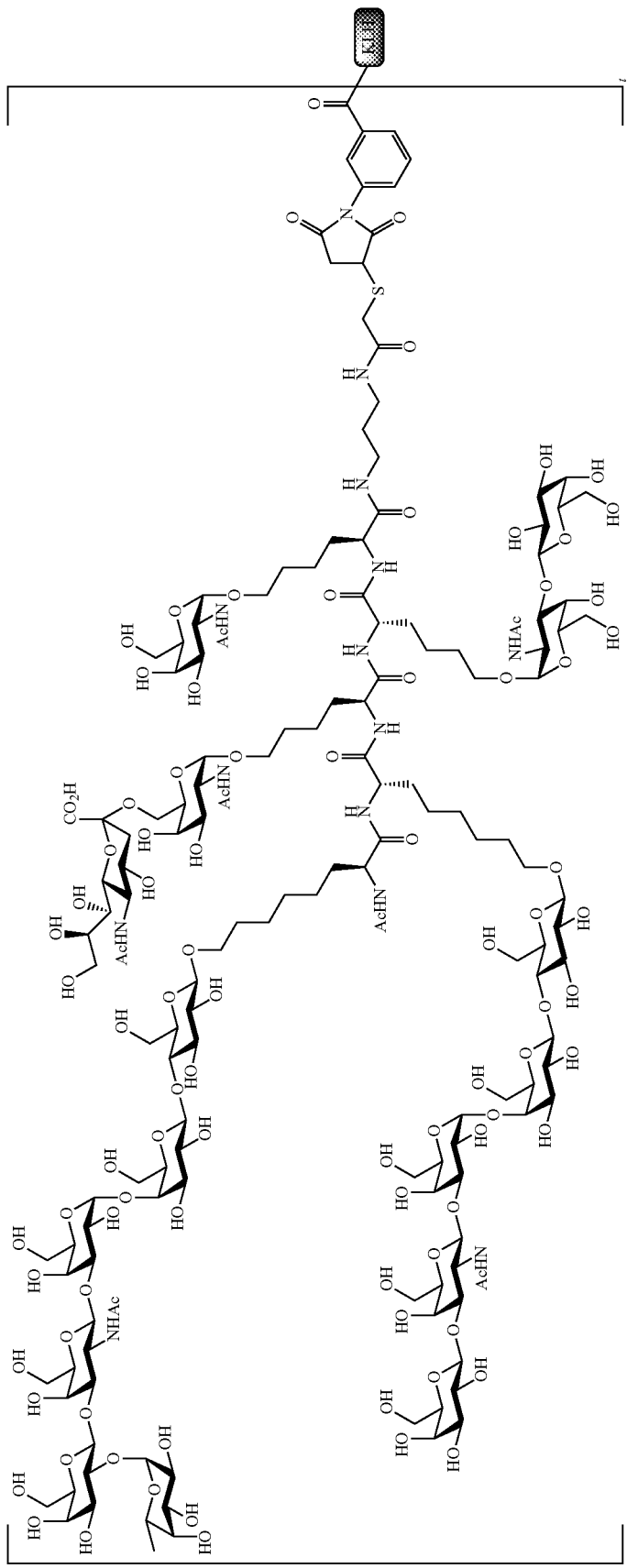

wherein t is as defined above and described in classes and subclasses herein.

In certain embodiments, the present invention provides methods of inducing antibodies in a subject, wherein the antibodies are capable of specifically binding with human tumor cells, which comprises administering to the subject any immunogenic glycoconjugate as described herein, wherein the immunogenic glycoconjugate comprises any multi-antigenic glycopeptide as described herein.

In some embodiments, the antibodies induced recognize at least one of the carbohydrate determinants selected from the group consisting of Globo-H, STN, Tn, TF, Gb5, and GM2. In some embodiments, a method of inducing antibodies comprises inducing a higher relative amount of IgG isotype antibodies as compared to IgM isotype antibodies. In certain embodiments, the antibodies generated recognize each of the carbohydrate determinants present on the glycopeptide.

Conjugates

In some embodiments, the present invention provides methods comprising the steps of:
(a) incubating an immunogenic carrier protein with a crosslinking agent to provide a crosslinking-ready immunogenic carrier protein;
(b) treating a thiol-containing biomolecule with a suitable disulfide reducing reagent; and
(c) combining the crosslinking-ready immunogenic carrier protein with the thiol-containing biomolecule under suitable conditions to provide an immunogenic carrier protein-biomolecule conjugate.

Alternatively and/or additionally to step (b), in certain embodiments provided methods include the step of freshly preparing a thiol-containing biomolecule prior to conjugation with crosslinking-ready immunogenic carrier protein. In certain embodiments, methods further comprise the step of removing unreacted crosslinking agent in step (a). In some embodiments, methods further comprise the step of removing unreacted biomolecule following conjugation step (c).

In some embodiments, the present invention provides methods comprising the steps of:
(a) treating a thiol-containing biomolecule with a suitable disulfide reducing reagent;
(b) incubating the thiol-containing biomolecule with a crosslinking agent to provide a crosslinking-ready biomolecule; and
(c) combining the crosslinking-ready biomolecule with an immunogenic carrier protein under suitable conditions to provide an immunogenic carrier protein-biomolecule conjugate.

Alternatively and/or additionally to step (b), in certain embodiments provided methods include the step of freshly preparing a thiol-containing biomolecule prior to incubating the thiol-containing biomolecule with a crosslinking agent. In certain embodiments, the methods further comprise the step of removing unreacted crosslinking agent in step (b).

In certain embodiments of conjugation methods described herein, the immunogenic carrier protein is selected from human serum albumin, bovine serum albumin, cationized bovine serum albumin, polylysine, OMPC, or KLH. In some embodiments, the immunogenic carrier protein is KLH.

In certain embodiments, a thiol-containing biomolecule is a glycopeptide. In some embodiments, a thiol-containing biomolecule is any glycopeptide described herein.

One of ordinary skill in the art will be familiar with a multitude of suitable crosslinking reagents for use in accordance with the provided methods. Such suitable crosslinking reagents are described in Hermanson, G. T. (2008). Bioconjugate Techniques. 2nd edition, Academic Press, New York. In certain embodiments, a crosslinking reagent is a heterobifunctional reagent. In certain embodiments, a crosslinking reagent is a homobifunctional reagent. In some embodiments, a bifunctional crosslinking reagent is selected from
i) maleimides (Bis-Maleimidoethane, 1,4-bismaleimidobutane, bismaleimidohexane, Tris[2-maleimidoethyl]amine, 1,8-bis-Maleimidodiethyleneglycol, 1,11-bis-Maleimidodiethyleneglycol, 1,4 bismaleimidyl-2,3-dihydroxybutane, Dithio-bismaleimidoethane,
ii) pyridyldithiols (1,4-Di-[3'-(2'-pyridyldithio)-propionamido]butane),
iii) aryl azides (Bis-[b-(4-Azidosalicylamido)ethyl]disulfide),
iv) NHS ester/maleimides (N-(a-Maleimidoacetoxy) succinimide ester, N-[β-Maleimidopropyloxy]succinimide ester, N-[g-Maleimidobutyryloxy]succinimide ester, N[g-Maleimidobutyryloxy]sulfosuccinimide ester, m-Maleimidobenzoyl-N-hydroxysuccinimide ester, m-Maleimidobenzoyl-N-hydroxysulfosuccinimide ester, Succinimidyl 4-[N-maleimidomethyl]cyclohexane-1-carboxylate, Sulfosuccinimidyl 4-[N-maleimidomethyl]cyclohexane-1-carboxylate, [N-e-Maleimidocaproyloxy]succinimide ester, [N-e-Maleimidocaproyloxy]sulfosuccinimide ester Succinimidyl 4-[p-maleimidophenyl]butyrate, Sulfosuccinimidyl 4-[p-maleimidophenyl]butyrate, Succinimidyl-6-[β-maleimidopropionamido]hexanoate, Succinimidyl-4-[N-Maleimidomethyl]cyclohexane-1-carboxy-[6-amidocaproate], N-[k-Maleimidoundecanoyloxy]sulfosuccinimide ester, succinimidyl-([N-maleimidopropionamido]-#ethyleneglycol) ester),
v) NHS ester/pyridyldithiols (4-Succinimidyloxycarbonyl-methyl-a-[2-pyridyldithio]toluene, 4-Sulfosuccinimidyl-6-methyl-a-(2-pyridyldithio)toluamidohexanoate),
vi) NHS ester/haloacetyls (N-Succinimidyl iodoacetate, Succinimidyl 3-[bromoacetamido]propionate, N-Succinimidyl[4-iodoacetyl]aminobenzoate, N-Sulfosuccinimidyl[4-iodoacetyl]aminobenzoate),
vii) pyridyldithiol/aryl azides (N-[4-(p-Azidosalicylamido) butyl]-3'-(2'-pyridyldithio)propionamide),
viii) maleimide/hydrazides (N-[β-Maleimidopropionic acid]hydrazide, trifluoroacetic acid salt, [N-e-Maleimidocaproic acid]hydrazide, trifluoroacetic acid salt, 4-(4-N-Maleimidophenyl)butyric acid hydrazide hydrochloride, N-[k-Maleimidoundecanoic acid]hydrazide),
ix) pyridyldithiol/hydrazides (3-(2-Pyridyldithio)propionyl hydrazide),
x) isocyanate/maleimides (N-[p-Maleimidophenyl]isocyanate), and 1,6-Hexane-bis-vinylsulfone, to name but a few.

Any suitable reducing agent may be used in accordance with the provided conjugation methods. In some embodiments, the step of treating a thiol-containing biomolecule with a suitable disulfide reducing reagent comprises a disulfide reducing agent selected from tris(2-carboxyethyl) phosphine) (TCEP), 2-mercaptoethylamine, cysteine, 2-mercaptoethanol (BME), or dithiothreitol (DTT). In some embodiments, a reducing agent is an immobilized reagent. In some embodiments, a reducing agent is TCEP gel.

In certain embodiments, provided conjugation methods have an efficiency of at least 200 biomolecules per immunogenic carrier protein. In certain embodiments, provided conjugation methods have an efficiency of at least 300, at least 400, at least 500, at least 600, at least 700, at least 800, at least 900, at least 1000, or at least 1100 biomolecules per immunogenic carrier protein. In certain embodiments, provided conjugation methods have an efficiency of about 200 to about 800 biomolecules per immunogenic carrier protein.

In certain embodiments, the present invention provides an improved bio-conjugation protocol that enables a significant increase in epitope ratio of bioconjugates. In certain embodiments, the present invention provides an immunogenic conjugate having the structure:

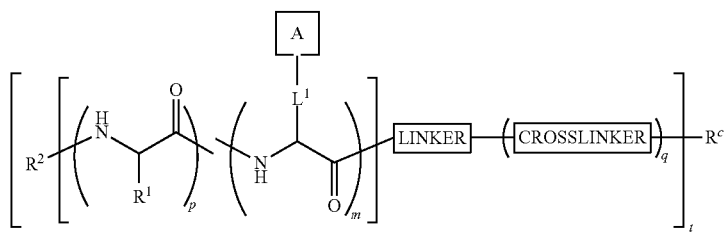

wherein each of $R^1$, $R^2$, $R^c$, $L^1$, A, p, m, q, the linker, and the crosslinker is as defined above and described in classes and subclasses herein;

each A is independently a carbohydrate determinant found on tumor cells;

t is the number of glycopeptide groups attached to the immunogenic carrier and is greater than 200. In certain embodiments, t is greater than 300, 400, 500, 600, 700, 800, 900, or 1000.

While not wishing to be bound by any particular theory, it is possible that the high epitope ratio (i.e., high values of t) of such conjugates correlates with enhanced immunogenicity of administered conjugates. Moreover, efficient production of antibodies in sera may help to eradicate tumor cells expressing corresponding carbohydrate antigents.

In certain embodiments, at least one occurrence of A is selected from Globo-H, STN, Tn, TF, Gb5, or GM2. In certain embodiments, each occurrence of A is selected from Globo-H, STN, Tn, TF, Gb5, or GM2. In certain embodiments, each occurrence of A is different.

In some embodiments, at least one occurrence of A comprises a disaccharide or larger carbohydrate. In some embodiments, each occurrence of A comprises a disaccharide or larger carbohydrate. In some embodiments, at least one occurrence of A comprises a trisaccharide or larger carbohydrate. In some embodiments, each occurrence of A comprises a trisaccharide or larger carbohydrate. In certain embodiments, at least one occurrence of A comprises a carbohydrate having a molecular weight greater than 350 daltons. In certain embodiments, at least one occurrence of A comprises a carbohydrate having a molecular weight greater than 500 daltons. In certain embodiments, at least one occurrence of A comprises a carbohydrate having a molecular weight greater than 750 daltons. In some embodiments, at least one occurrence of A is Globo-H, Gb5, or GM2.

In certain embodiments, a crosslinker is derived from any bifunctional crosslinking reagent described above.

Linkers

In certain embodiments of the methods, glycopeptides, and glycoconjugates described above, a linker is a covalent bond. In some embodiments, a linker is a linear or branched chain alkyl or aryl carboxylic ester, or an optionally substituted, bivalent $C_{1-10}$ saturated or unsaturated, straight or branched, hydrocarbon chain, wherein one to six methylene units of the chain are independently replaced by —S—, —NR—, —N(R)C(O)—, —C(O)N(R)—, —O—, or —C(O)—. In certain embodiments, a linker is —NH(CH$_2$)$_{2-5}$NHC(O)CH$_2$S—. In some embodiments, a linker is —NH(CH$_2$)$_3$NHC(O)CH$_2$S—.

Crosslinkers

In certain embodiments of the methods, glycopeptides, and glycoconjugates described above, a crosslinker is a moiety derived from a bifunctional crosslinking reagent as described above. In some embodiments, a crosslinker is a moiety derived from a bifunctional crosslinking reagent capable of conjugating a surface amine of a carrier and a thiol of a linker. In certain embodiments, a crosslinker is a moiety derived from a bifunctional crosslinking reagent capable of conjugating a surface hydroxyl of a carrier and a thiol of a linker. In some embodiments, a crosslinker is a moiety derived from a bifunctional crosslinking reagent capable of conjugating a surface thiol of a carrier and a thiol of a linker. In some embodiments, a crosslinker is a moiety derived from a bifunctional crosslinking reagent capable of conjugating a surface carboxyl of a carrier and a thiol of a linker. In some embodiments, a crosslinker is a moiety having the structure:

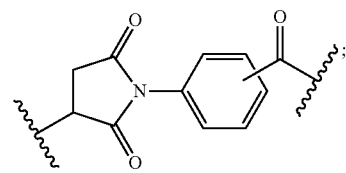

whereby said structure is generated upon conjugation of a maleimidobenzoic acid N-hydroxy succinimide ester with a linker.

Formulations

As described above, the present invention provides compounds and synthetic methodologies useful in the development of novel therapeutic agents, particularly for fully synthetic cancer vaccines and/or therapeutics. In general, the compounds and glycopeptides prepared as disclosed herein can be conjugated to a protein carrier or a lipid to generate useful glycoconjugates for the treatment and/or prevention, (preferably the prevention of the recurrence), of cancer in a subject suffering therefrom. In addition, glycoconjugates prepared by processes disclosed herein are useful in adjuvant therapies as vaccines capable of inducing antibodies immunoreactive with various tumor cells. Such adjuvant therapies may reduce the rate of recurrence of certain cancers, and increase survival rates after surgery. Clinical trials on patients surgically treated for cancer who are then treated with vaccines prepared from a cell surface differentiation antigen found in patients lacking the antibody prior to immunization, a highly significant increase in disease-free interval may be observed (P. O. Livingston, et al., *J. Clin. Oncol.*, 1994, 12, 1036).

Thus, the present invention provides pharmaceutical compositions for treating cancer and/or for preventing the recurrence of cancer, comprising any compound of the present invention disclosed herein, as an active ingredient, optionally in combination with a pharmaceutically acceptable carrier. Pharmaceutical compositions of the present invention may further comprise other therapeutically active ingredients (e.g., chemotherapeutic and/or palliative). For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

In certain embodiments, pharmaceutical compositions or methods of the invention comprise an immunological adjuvant, or a combination of immunological adjuvants.

In certain embodiments, the adjuvant is a saponin adjuvant (see, e.g., Marciani et al., *Vaccine*, 2000, 18, 3141, U.S. Pat. Nos. 6,080,725 and 5,977,081, the entire contents of which are hereby incorporated by reference). One example of a saponin adjuvant includes, but is not limited to, GPI-0100, (Galenica Pharmaceuticals, Inc., Frederick, Md.) which is a semi-synthetic adjuvant derived by modifying selected natural saponins

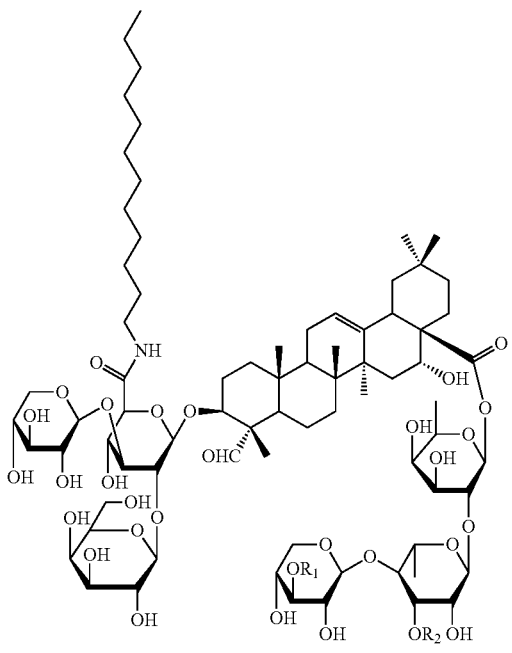

GPI-0100

Saponins isolated from *Quillaja soponaria Molina* contain two acyl moieties, a normonoterpene carboxylic acid and a normonoterpene carboxylic acid glycoside, which are linked linearly to a fucosyl residue attached at position C-28. It has been hypothesized that these lipophilic acyl groups may be responsible for these saponins' toxicity and their ability to stimulate cytotoxic T cells against exogenous antigens. The linkage between the fucosyl residue and the acyl group is unstable and hydrolyzes under mild conditions (pH≥6) with concomittant loss of saponins capability to stimulate cell-mediated immune response. Unlike their saponin precursors, GPI-0100 adjuvants comprise a stable non-toxic lipophilic moiety in the saponin's glucuronic residue. Methods for preparing these semi-synthetic adjuvants are well-known in the art. For example, GPI-0100 adjuvants may be prepared by hydrolizing quillaja saponins (which are commercially available) under basic conditions to yield the corresponding deacylated product. The deacylated intermediate may then be reacted with a suitable amine reagent using standard carboxylic acid moiety activation methodology to give the desired compounds. A wide variety of procedures are effective for extrating saponin compounds. They are generalized as follows: (i) defatting of the organic matter with a hydrophobic organic solvent such as petroleum ether; (ii) extraction with a suitable alcohol (e.g., methanol or ethanol) or alcohol-water mixture; (iii) evaporation of the carinol solvent; and (iv) partitioning of the dried alcohol extract between water and n-butanol saturated with water, followed by precipitation of the crude saponins from the n-butanol/water with a suitable organic solvent (e.g., diethyl ether). Purification of the saponin extract may require multiple separation steps. For example, preliminary fractionation may be carried out using conventional open column chromatography or flash chromatography on silica gel, in combination with a more sophisticated chromatographic technique such as High Pressure Liquid Chromatography (HPLC), droplet counter-current liquid chromatography (DCCC) or centrifugal Liquid Chromatography (RLCC). The integration of these techniques with preparative TLC typically affords separated and purified saponins.

In certain embodiments, the adjuvant is or comprises bacteria or liposomes. In certain exemplary embodiments, the adjuvant includes but is not limited to, *Salmonella minnesota* cells, bacille Calmette-Guerin, GPI-0100, or QS-21.

Compounds of the present invention may be combined with a pharmaceutically acceptable carrier to form a pharmaceutical composition. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. In certain embodiments, the pharmaceutical composition includes a pharmaceutically acceptable amount of an inventive compound. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, from about 5% to about 70%, or from about 10% to about 30%.

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such carriers as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

Drug-eluting forms include coated or medicated stents and implantable devices. Drug-eluting stents and other devices may be coated with a compound or pharmaceutical preparation and may further comprise a polymer designed for time-release.

In certain embodiments, a compound or pharmaceutical preparation is administered orally. In other embodiments, the compound or pharmaceutical preparation is administered intravenously. In certain embodiments, a compound is attached via a cleavable linker to a solid support that is administered with a catheter. Alternative routes of administration include sublingual, intramuscular, and transdermal administrations.

When the compounds of the present invention are administered as pharmaceuticals, to humans and animals, they can be given per se or as a pharmaceutical composition containing, for example, 0.1% to 99.5%, or 0.5% to 90%, of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

These compounds may be administered to humans and other animals for therapy by any suitable route of administration, including orally, nasally, as by, for example, an aerosol, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. Preferred chronic treatments involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six, or more sub-doses administered separately at appropriate intervals throughout the day, optionally, in unit dosage forms.

While it is possible for a compound of the present invention to be administered alone, it is preferable to administer the compound as a pharmaceutical formulation (composition) as described above.

The compounds according to the invention may be formulated for administration in any convenient way for use in human or veterinary medicine, by analogy with other pharmaceuticals.

The invention provides kits comprising pharmaceutical compositions of an inventive compound. In certain embodiments, such kits include the combination of a compound of the present invention and another chemotherapeutic agent. The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. The kit may include a full cycle of chemotherapy. In certain embodiments, the kit includes multiple cycles of chemotherapy.

Uses

The current standard treatment for patients with advanced ovarian cancer consists of aggressive cytoreductive surgery followed by taxane and platinum-based chemotherapy. Patients with ovarian, fallopian tube or primary peritoneal cancer have an 80% chance of obtaining a clinical response to primary taxane and platinum based chemotherapy, and a significant proportion will enter a complete clinical remission at the conclusion of therapy. While the median overall survival for optimally debulked patients has increased to 65.6 months, less than 30% of patients remain free of disease, and 10% of patients with suboptimally debulked disease will remain disease free with a progression free interval of 24 and 18 months respectively (Armstrong D K, Bundy B, Wenzel L, et al *N Engl J Med* 354:34-43, 2006). Patients with recurrence generally have subsequent responses of limited duration and eventually develop resistant disease (Markman M, Markman J, Webster K, et al. *J Clin Oncol* 22:3120-5, 2004). Options to prolong remission and/or to prevent relapse are needed and provided by the present invention.

Immune directed therapy represents an attractive investigational treatment strategy for patients who are in clinical remission where disease burden is lowest (Sabbatini P, Spriggs D R. *J Clin Oncol* 24:537-9, 2006). Preclinical models have demonstrated the clearance of circulating tumor cells and the elimination of systemic micrometastasis with both passively administered and vaccine induced antibodies (Zhang H, Zhang, S, Cheung N K, et al. Vaccine 23:3114-22, 2005; Ragupathi G, Gathuru J, Livingston P. Cancer Treat Res 123:157-80, 2005).

In certain embodiments, a method of treatment is provided comprising administering to the subject a therapeutically effective amount of any of the glycoconjugates disclosed herein, optionally in combination with a pharmaceutically acceptable carrier. In some embodiments, the method further comprises co-administering an immunological adjuvant (defined further below), or a combination of immunological adjuvants. In certain embodiments, the cancer is a solid tumor or an epithelial tumor. As mentioned above, methods for the treatment of cancer and/or for the prevention of recurrence of cancer are provided, which comprises administering to the subject an amount of any of the glycoconjugates disclosed above effective to induce antibodies. Also provided are methods for inducing antibodies in a human subject, wherein the antibodies are capable of specifically binding with human tumor cells. In certain embodiments, a carbohydrate antigen is linked to an immunogenic carrier either directly or through a crosslinker, wherein the carrier is a protein, peptide or lipid. In certain embodiments, a carrier is human serum albumin, bovine serum albumin, cationized bovine serum albumin, polylysine, OMPC, or KLH. In certain embodiments, the carrier is a lipid having the structure:

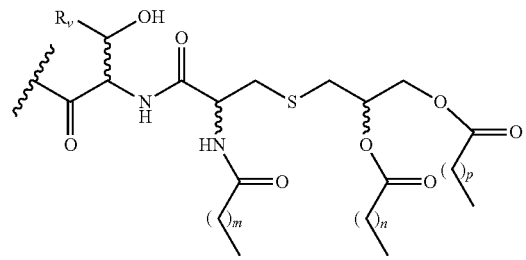

wherein m', n' and p' are each independently integers between about 8 and 20; and $R_{V}$ is hydrogen, substituted or unsubstituted linear or branched chain lower alkyl or substituted or unsubstituted phenyl. In certain exemplary embodiments, m', n' and p' are each 14 and the lipid is tripalmitoyl-S-glycerylcysteinylserine (e.g., PamCys).

In certain embodiments, a provided method comprises administering to the subject a therapeutically effective amount of any of the compounds and/or glycopeptides disclosed herein, in combination with an immunogenic carrier, optionally in combination with a pharmaceutically acceptable carrier. Specifically, in certain embodiments, a provided method comprises administering a carbohydrate antigen conjugated to an immunogenic carrier. In certain embodiments, a provided method comprises administering a carbohydrate antigen and an immunogenic carrier that have not been conjugated. Rather, they are administered concurrently, or successively, as separate entities.

For the purpose of the invention, a compound/glycopeptide and a carrier are said to be administered concurrently when they are administered (i) as a single composition containing the compound/glycopeptide and the carrier, (ii) as two separate compositions or (iii) are delivered by separate routes within a short enough period of time that the effective result is equivalent to that obtained when both compound/glycopeptide and carrier are administered as a single composition.

In certain embodiments, the present disclosure provides methods of eliciting antibodies in a subject comprising administering to the subject a construct of the present disclosure. In some embodiments, the present invention provides methods of inducing antibodies which further comprise co-administering an immunological adjuvant, or a combination of immunological adjuvants. In certain embodiments, an adjuvant is a saponin adjuvant. In certain other embodiments, an adjuvant is bacteria or liposomes. In certain embodiments, the adjuvant includes but is not limited to, *Salmonella minnesota* cells, bacille Calmette-Guerin, GPI-0100, or QS21. Specifically, when a multi-antigenic glycopeptide comprising at least two different antigenic domains is used, it is possible to induce at least two different types of antibodies. In certain embodiments, each antigen present on the glycopeptide elicits an antibody type specific to that antigen. In certain embodiments, the antibodies produced are those that recognize at least one antigen present on the glycopeptide. In certain embodiments, an inventive multi-antigenic glycopeptide, when administered to a subject, produces antibodies to a subset of the antigens present on the glycopeptide backbone. In certain embodiments, some of the antibodies produced recognize two or more antigens of the glycopeptide. In certain embodiments, the inventive glycopeptides comprise carbohydrate domains, or truncated or elongated versions thereof, that are found on tumor cells.

Compounds of the present invention may be used in vitro or in vivo. The inventive compounds may be particularly useful in the treatment of neoplasms or other proliferative diseases in vivo. However, inventive compounds described above may also be used in vitro for research or clinical purposes (e.g., determining the susceptibility of a patient's disease to an inventive compound, researching the mechanism of action, elucidating a cellular pathway or process).

In some embodiments, compounds of the present invention are provided for use in medicine. In some embodiments, the present invention provides a method of treating a proliferative disease in a subject suffering therefrom, the method comprising administering to the subject a therapeutically effective amount of an inventive compound. In certain embodiments, the proliferative disease is a benign neoplasm. In certain embodiments, the proliferative disease is cancer.

Compounds of the present invention may be used in the treatment or prevention of neoplasms. In certain embodiments, the neoplasm is a benign neoplasm. In other embodiments, the neoplasm is a malignant neoplasm.

In some embodiments, the cancer is a hematological malignancy. In certain embodiments, the cancer is a solid tumor. Exemplary cancers that may be treated using inventive compounds include colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, neuroendocrine cancer, breast cancer, gastric cancer, eye cancer, gallbladder cancer, laryngeal cancer, oral cancer, penile cancer, glandular tumors, rectal cancer, small intestine cancer, sarcoma, carcinoma, melanoma, urethral cancer, vaginal cancer, to name but a few. In some embodiments, the cancer is small cell lung cancer. In some embodiments, the cancer is ovarian cancer. In some embodiments, the cancer is breast cancer. In some embodiments, the cancer is lung cancer. In some embodiments, the cancer is of endometrial origin. In some embodiments, the cancer is of epithelial origin. In some embodiments, the cancer is colon cancer. In some embodiments, the cancer is prostrate cancer. In some embodiments, the cancer is gastric cancer. In some embodiments, the cancer is pancreatic cancer. In some embodiments, the cancer is peritoneal cancer. In some embodiments, the cancer is cancer of the fallopian tube. In some embodiments, the cancer originates from any one of the above-mentioned organs or tissues.

In certain embodiments, compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or anticancer agents that may be used in combination with compounds of the present invention include surgery, radiotherapy (γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. Additionally, the present invention also encompasses the use of certain cytotoxic or anticancer agents currently in clinical trials and which may ultimately be approved by the FDA (including, but not limited to, epothilones and analogues thereof and geldanamycins and analogues thereof). For a more comprehensive discussion of updated cancer therapies see, www.nci.nih.gov and The Merck Manual, Seventeenth Ed. 1999, the entire contents of which are hereby incorporated by reference.

In certain embodiments, inventive compounds are useful in treating a subject in clinical remission. In some embodiments, the subject has been treated by surgery and may have limited unresected disease.

EXEMPLIFICATION

Example 1

Synthesis of a Unimolecular Pentavalent Vaccine Construct Containing Globo-H, GM2, STn, TF and Tn

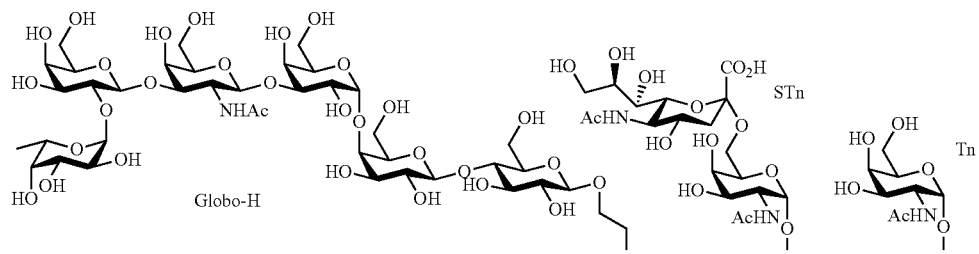

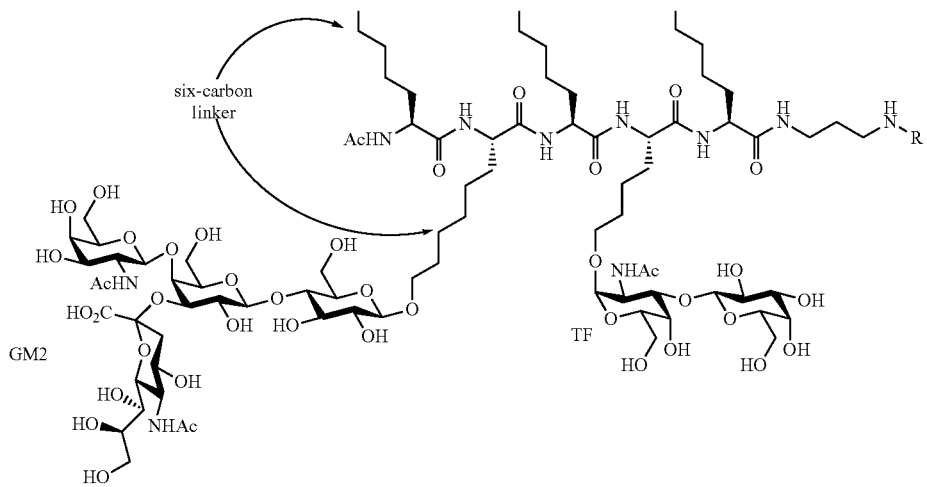

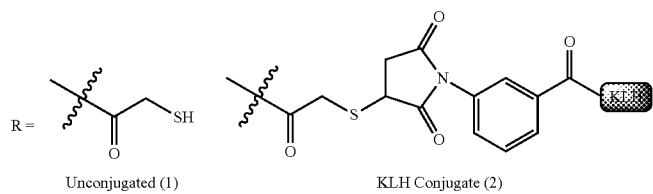

Unconjugated (1)          KLH Conjugate (2)

Unimolecular Pentavalent Construct KLH Conjugate (2).

This Example describes the preparation of the conjugate (2). In earlier studies, a structurally related first-generation unimolecular pentavalent construct had been conjugated to KLH carrier protein with a conjugation efficiency of 228 glycopeptides per KLH (Keeling, S. J.; Danishefsky, S. J. Proc. Natl. Acad. Sci. USA. 2004, 101, 11937; Ragupathi 2006, supra; Biswas K, Coltart D M, Danishefsky S J. Tetrahedron Lett 3:6107-10, 2002; Cho Y S, Wan Q, Danishefsky S J. Bioorg Med Chem 13:5259-66, 2005; Wan Q, et al. Olefin Cross-Metathesis: A powerful tool for constructing vaccines composed of multimeric antigens. J Carbohydrate Chem 24:425-40, 2005; Keding S J, et al. Tetrahedron Lett 44:3413-16, 2003; Keding S J, Edno A, Danishefsky S J. Tetrahedron 59:7023-31, 2003; Cho S C et al. Bioorg. Med. Chem. 13, 5259-5266, 2005). Realizing that it is desirable to generate a more robust immune response by obtaining a higher epitope/KLH ratio for the conjugate (2), Applicant developed a new procedure for conjugation as described below.

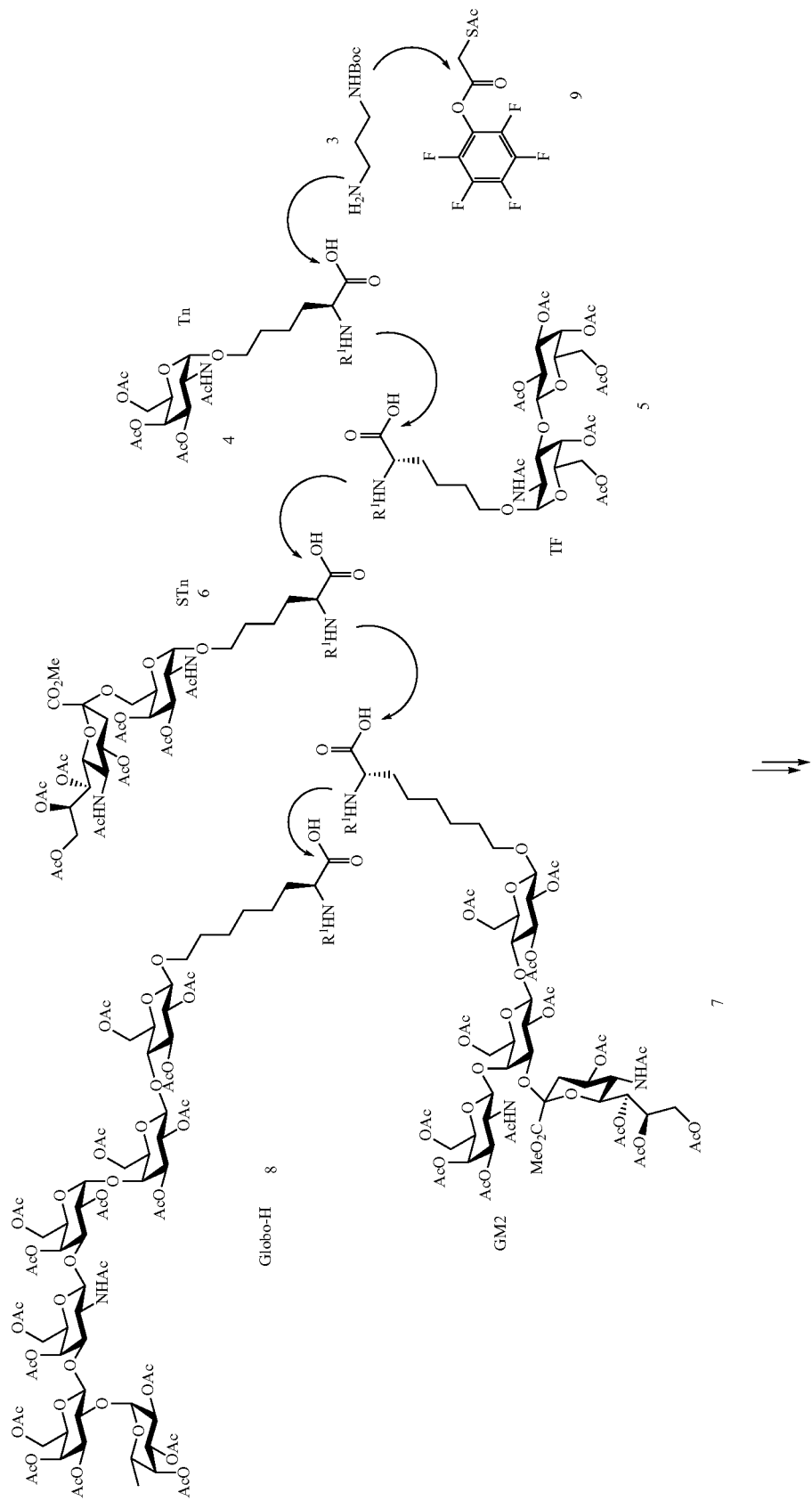
Scheme 1. Synthesis of conjugate 2 containing Globo-H, GM2, STn, TF and Tn

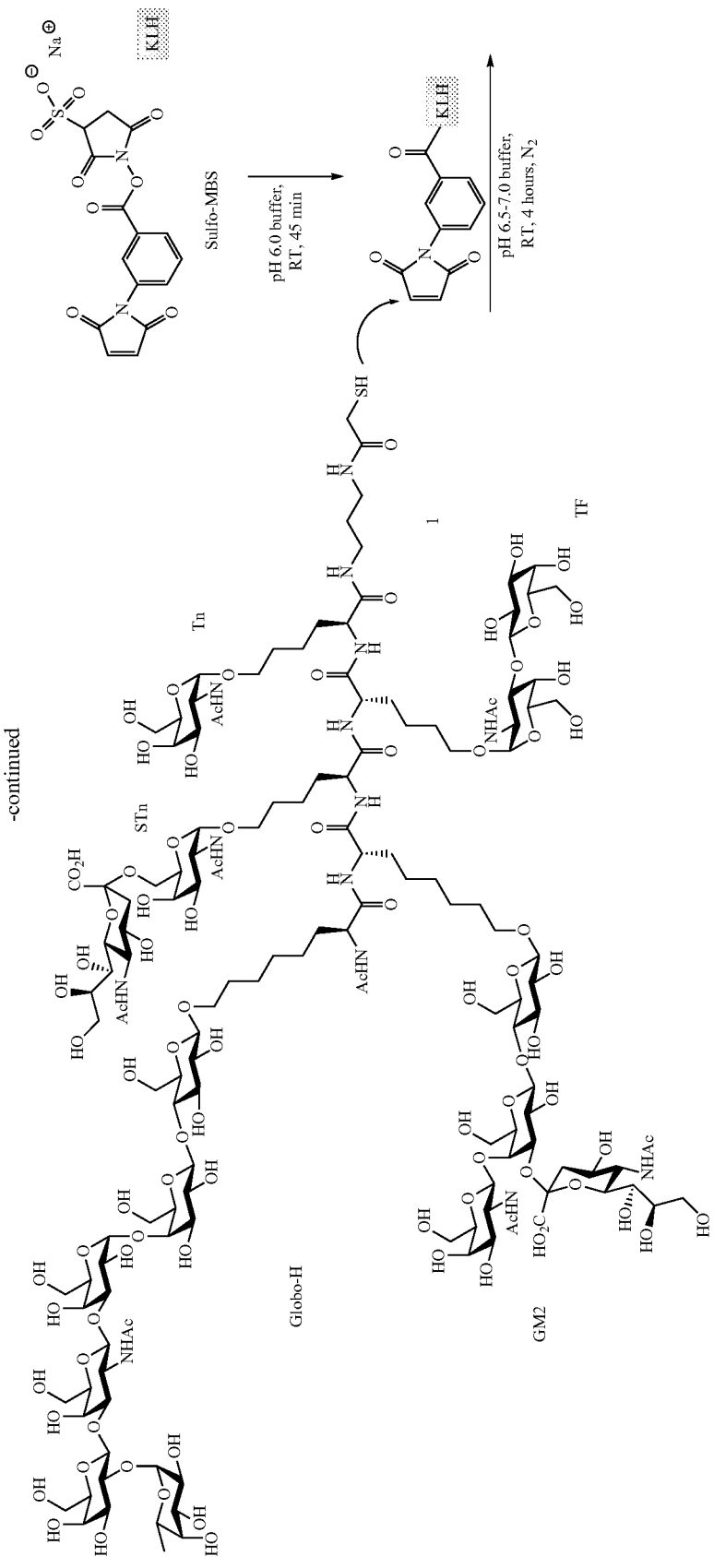

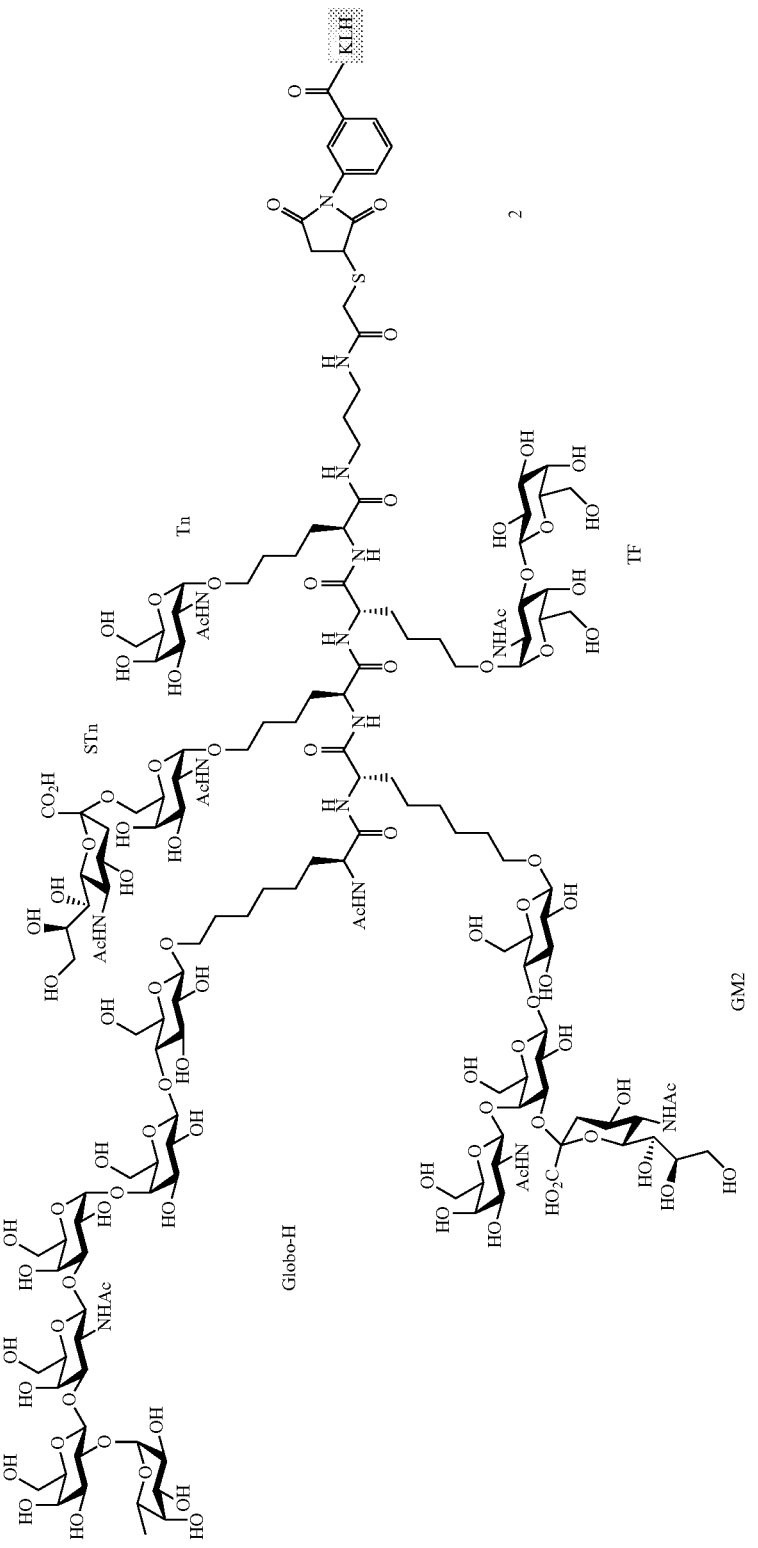

Carrier protein KLH was first incubated with sulfo-MBS (m-maleimidobenzoyl-N-hydroxysuccinimide) in pH 6.0 phosphate buffer for one hour. Next, the unconjugated Sulfo-MBS was eliminated by passage over a G25 Sephadex column and maleimide-activated KLH was then obtained. Glycopeptide construct 1 (freshly prepared, passed through TCEP gel immediately prior to use) was mixed with freshly prepared maleimide-activated KLH in pH 6.5-7.0 phosphate buffer and stirred at room temperature for 4 hours. Following incubation, unreacted glycopeptide was removed using a 30,000 molecular weight cut off Pellicon XL filter (Millipore). Finally the corresponding KLH conjugate 2 was obtained as a phosphate buffer solution.

The number of copies of glycopeptide construct incorporated in the KLH conjugate was determined to be 505 per KLH by hydrolytic carbohydrate analysis (Lloyd, K. O.; Savage, A. *Glycoconjugate J.* 1991, 8, 439; Hardy, M. R.; Townsend, R. R. *Proc. Natl. Acad. Sci. USA* 1988, 85, 3289) and standard protein analysis (Bio-Rad dye-binding method). The conjugation yield was 50% with respect to the unimolecular pentavalent glycopeptide construct, and the recovery yield of KLH was ca. 98%. This modified procedure had thus provided a much more efficient conjugation loading than the previous one (228/1). While not wishing to be bound by any particular theory, it is possible that the use of freshly prepared glycopeptide construct 1, which contains a highly oxidizable mercapto group, is useful in achieving such a high epitope ratio. One of the known possible oxidations of the sensitive mercapto group results in formation of its putative dimer, via disulfide formation. It is therefore useful to pass this construct through TCEP gel immediately prior to use, in order to reduce the dimer and allow recovery of the glycopeptide construct 1. Preservation of the intact mercapto group is important for the subsequent bio-conjugation reaction, which presumably proceeds via Michael addition to the maleimide. With the pentavalent conjugate 2 in hand, immunological studies in preclinical mouse settings were done as described in Example 2.

Example 2

This Example describes biological studies of the conjugate described in Example 1 (Zhu, J. et al., J. Am. Chem. Soc. 131, 9298-9303, 2009).

Animal Immunizations.

Group of five mice (female; C57BL/6J) were immunized subcutaneously at one site with vaccine (2), containing 10 µg of unimolecular pentavalent construct (UPC) plus 20 µg of QS-21 adjuvant in 200 µL PBS, at 0, 1, 2 and 5 weeks. "Pre-treatment" serum was taken one week before the first vaccination. "Post" serum was taken one week after the third vaccination. "Boost" serum was taken one week after the fourth vaccination.

Serum ELISA Assay.

Enzyme-linked immunosorbent assays (ELISA) were performed, as described previously (Ragupathi, G.; Cappello, S.; Yi, S. S.; Canter, D.; Spassova, M.; Bornmann, W. G.; Danishefsky, S. J.; Livingston, P. O. *Vaccine* 2002, 20, 1030. (b) Ragupathi, G.; Koide, F.; Sathyan, N.; Kagan, E.; Spassova, M.; Bornmann, W.; Gregor, P.; Reis, C. A.; Clausen, H.; Danishefsky, S. J.; Livingston, P. O. *Cancer Immunol. Immunother.* 2003, 52, 608), to determine the IgM and IgG serum antibody titers achieved associated with each of the individual carbohydrate antigens (Globo-H, GM2, STn, TF and Tn). In particular, Globo-H ceramide, GM2 ceramide, Gb5 ceramide, Gb5-lipid (see Examples 4 and 5), ovine submaxillary mucin (OSM, expressing sTn), desialylated porcine submaxillary mucin (dPSM expressing TF), and desialylated ovine submaxillary mucin (dOSM, expressing Tn), were each coated on ELISA plates at an antigen dose of 0.1 µg/well, and were incubated overnight at 4° C. Nonspecific sites were blocked with 3% human serum albumin (HSA) for 2 h, and serially diluted antiserum was added to each well. After 1 h of incubation, the plates were washed, and alkaline phosphatase labeled goat anti-mouse IgM or IgG was added at 1:200 dilution (Southern Biotechnology Associates Inc., Birmingham, Ala.). The antibody titer was defined as the highest dilution with absorbance of 0.1 or greater over that of normal control mouse sera.

As shown in Table 1 and FIG. 1, pre-vaccination sera from none of the five mice showed reactivity against the five antigens in the vaccine. Post-immunization sera from mice immunized with the compound 2 vaccine plus QS-21 adjuvant produced substantial titers of antibodies corresponding to each of the five carbohydrate antigens: Globo-H ceramide, GM2 ceramide, STn (OSM), TF (dPSM) and Tn (dOSM). Unlike a previous first-generation unimolecular pentavalent construct KLH conjugate, which did not successfully induce antibodies against one of the antigens (Lewis[y]), this second-generation construct, conjugate 2 did produce excellent IgG and IgM antibody titers against all five antigens, including the GM2 antigen, which replaced Lewis[y] in this construct. Since GM2 is an important epitope that is over-expressed on prostate and breast cancer cell lines (Livingston, P. O.; Natoli, E. J.; Calves, M. J.; Stockert, E.; Oettgen, H. F.; Old, L. *J. Proc. Natl. Acad. Sci. USA* 1987, 84, 2911; Livingston P. O.; Wong, G. Y.; Adluri, S.; Tao, Y.; Padavan, M.; Parente, R.; Hanlon, C.; Calves, M. J.; Helling, F.; Ritter, G. *J. Clin. Oncol.* 1994, 12, 1036), Applicant sought to incorporate GM2 into the construct in order to greatly enhance the immunogenicity of the conjugate 2. All of the data indicate that the immunological properties of the individual carbohydrate antigens are preserved in the context of these highly complex vaccine constructs.

TABLE 1

Antibody titers by Enzyme-Linked ImmunoSorbent Assay (ELISA)[a]

| Mouse # | Globo-H Ceramide | | GM2 Ceramide | | OSM for sTn | | dPSM for TF | | dOSM for Tn | |
|---|---|---|---|---|---|---|---|---|---|---|
| | IgG | IgM | IgG | IgM | IgG | IgM | IgG | IgM | IgG | IgM |
| Pre-Serum | 0 | 0 | 0 | 0 | 0 | 0 | 0 | 160 | 0 | 0 |
| 1 | 160 | 160 | 160 | 0 | 400 | 320 | 400 | 400 | 800 | 0 |
| 2 | 640 | 160 | 640 | 0 | 1600 | 40 | 400 | 400 | 1600 | 0 |
| 3 | 640 | 160 | 640 | 0 | 800 | 320 | 200 | 100 | 6400 | 200 |
| 4 | 640 | 640 | 2560 | 0 | 1600 | 2560 | 1600 | 800 | 3200 | 400 |

TABLE 1-continued

Antibody titers by Enzyme-Linked ImmunoSorbent Assay (ELISA)[a]

| Mouse # | Globo-H Ceramide | | GM2 Ceramide | | OSM for sTn | | dPSM for TF | | dOSM for Tn | |
|---|---|---|---|---|---|---|---|---|---|---|
| | IgG | IgM | IgG | IgM | IgG | IgM | IgG | IgM | IgG | IgM |
| 5 | 640 | 160 | 640 | 0 | 1600 | 20 | 1600 | 800 | 1600 | 400 |
| Median | 640 | 160 | 640 | 0 | 1600 | 320 | 800 | 400 | 1600 | 200 |

[a]IgM or IgG antibody reciprocal titers of pre- and post-vaccination sera tested for the five antigens in the pentavalent vaccines. ELISA assays were performed to determine IgM and IgG serum antibody titers as previously described (Ragupathi 2002 & 2003, supra). In brief, Globo-H ceramide, GM2 ceramide, ovine submaxillary mucin (OSM expressing sTn), desialylated ovine submaxillary mucin (dOSM expressing Tn), or desialylated porcine submaxillary mucin (dPSM expressing TF) was coated on ELISA plates at an antigen dose of 0.1 μg/well and incubated overnight at 4° C. Nonspecific sites were blocked with 1% human serum albumin (HSA) for 2 h, and serially diluted antiserum was added to each well. After 1 h of incubation, the plates were washed, and alkaline phosphatase labeled goat anti-mouse IgM or IgG was added at 1:400 dilution (Southern Biotechnology Associates Inc., Birmingham, AL). The antibody titer was defined as the highest dilution with absorbance of 0.1 or greater over that of normal control mouse sera.

Flow Cytometry.

The cell surface reactivity of the antibodies induced by the conjugate 2 vaccine was determined by FACS assay analysis with MCF-7 breast cancer cells, as described previously (Sabbatini, P. J.; Kudryashov, V.; Ragupathi, G.; Danishefsky, S. J.; Livingston, P. O.; Bornmann, W.; Spassova, M.; Zatorski, A.; Spriggs, D.; Aghajanian, C.; Soignet, S.; Peyton, M.; O'Flaherty, C.; Curtin, J.; Lloyd, K. O. *Int. J. Cancer.* 2000, 87, 79). Single-cell suspensions of $5 \times 10^5$ cells/tube were washed in phosphate-buffered saline with 3% fetal calf serum, and then incubated with 20 μL of 1/200 diluted antisera for 30 min on ice. A total of 20 μL of 1/15 goat anti-mouse IgG or IgM labeled with FITC was added, and percent positive cells and mean fluorescent intensity (MFI) of stained cells were analyzed using a FACScan (Becton Dickinson, San Jose, Calif.).

The post- and boost-vaccination sera flow cytometry results for the five mice receiving vaccine 2 are described in Table 2. Serologic responses to these vaccinations were almost exclusively IgM. As shown, the median percentage of positive cells in the post-vaccination serum increased from 10% to 36%, and the mean fluorescent intensity (MFI) increased from 85 to 302. The boost-vaccination serum showed a further increase in percentage of positive cells to 70%, with an MFI increase to 486. These experimental results suggest that conjugate 2 may indeed be a very effective and clinically useful vaccine candidate, especially in conjunction with boost-injection.

TABLE 2

Antibody Binding Studies by Fluorescence-Activated Cell Sorting (FACS)[a]

| | Post-Vaccination Serum MCF-7 Cells (Breast Cancer) | | | | Boost-Vaccination Serum MCF-7 Cells (Breast Cancer) | | | |
|---|---|---|---|---|---|---|---|---|
| | IgM | | IgG | | IgM | | IgG | |
| Mouse # | % Pos | MFI | % Pos | MFI | % Pos | MFI | % Pos | MFI |
| Pre-Serum | 10% | 85 | 10% | 64 | 10% | 85 | 10% | 64 |
| 1 | 53% | 302 | 14% | 87 | 70% | 561 | 8% | 55 |
| 2 | 33% | 203 | 8% | 78 | 72% | 486 | 1% | 33 |
| 3 | 36% | 313 | 16% | 245 | 72% | 897 | 3% | 41 |
| 4 | 49% | 321 | 8% | 52 | 51% | 424 | 3% | 20 |
| 5 | 34% | 195 | 10% | 55 | 56% | 450 | 10% | 68 |
| Median | 36% | 302 | 10% | 78 | 70% | 486 | 3% | 41 |

[a]IgM and IgG FACS profiles for the five mice immunized with 5 μg of unimolecular pentavalent-KLH vaccine plus QS-21 tested on MCF-7 breast cancer cell lines. Pre-, post- and boost-vaccination results shown, % positive cells (MFI). FACS analysis (v(a)): MCF-7 human breast cancer cells expressing all five antigens (but especially globo H). Single-cell suspensions of $5 \times 10^7$ cells/tube were washed in phosphate-buffered saline with 3% fetal calf serum and incubated with 20 μL of 1/200 diluted antisera for 30 min on ice. A total of 20 μL of 1/15 goat anti-mouse IgG or IgM labeled with FITC was added, and percent positive cells and mean fluorescent intensity (MFI) of stained cells were analyzed using a FACScan (Becton Dickinson, San Jose, CA). Pre-, post- and boost-vaccination sera were analyzed together, and the pretreatment percent positive cells gaited at 10%. Results were considered positive when percent positive cells was 3-fold the negative controls (>30% positive cells) and the MFI was 150% or more of the negative control MFI.

Example 3

Synthesis of the Gb5 Glycoamino Acid 10

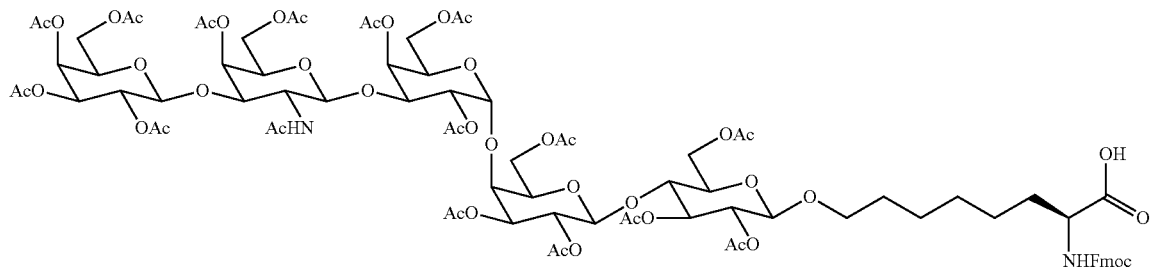

Synthesis of Ethanethiosulfonamide 12

To a stirred mixture of the glycal 11 (2.0 g, 2.63 mmol), benzenesulfonamide (2.48 g, 15.8 mmol), and freshly activated powdered 4 Å MS (2 g) in dry ether (80 mL) at −8° C. was added hsym-coll)$_2$ClO$_4$ (4.92 g, 10.5 mmol). The resulting mixture was stirred overnight in the dark at −8° C. and quenched with Na$_2$S$_2$O$_3$ solution (100 mL). After filtration and extraction with ether (3×60 mL), the combined organic layer was washed with saturated CuSO$_4$ solution (100 mL) and brine (50 mL), dried over MgSO$_4$, and concentrated in vacuo. The crude product was subjected to the next reaction without further purification. To a solution of ethanethiol (1.94 mL, 26.2 mmol) in anhydrous DMF (10 mL) at −40° C. was added LHMDS (13.3 mL, 1.0 M in THF). After 5 min of stirring, reaction mixture was transferred via a cannula to a flask containing of iodosulfonamide (crude) in DMF (40 mL) at −40° C. The reaction mixture was slowly warmed to 0° C. and stirred for total 3 h. After dilution with ether (300 mL), the organic layer was washed with NH$_4$Cl solution (50 mL), and brine, dried over MgSO$_4$, and concentrated under reduced pressure. Flash column chromatography using 10:1-7:1 hexane/EtOAc gave 12 (900 mg, 35%) as a white foam and recovery starting material (420 mg). $^1$H NMR (500 MHz, CDCl$_3$) δ7.92 (dd, 2H, J=7.2 Hz, J=1.3 Hz), 7.58-7.55 (m, 1H), 7.51-7.47 (m, 2H), 5.39 (bs, 1H), 5.09 (d, 1H, J=9.0 Hz), 4.67 (bd, 1H, J=8.9 Hz), 4.49 (d, 1H, J=3.0 Hz), 4.48 (d, 1H, J=1.5 Hz), 4.31 (d, 1H, J=10.1 Hz), 4.25 (dd, 1H, J=9.0 Hz, J=5.4 Hz), 4.09 (s, 1H), 3.92 (dd, 1H, J=9.1 Hz, J=5.9 Hz), 4.09 (t, 1H, J=2.6 Hz), 3.92 (dd, 1H, J=9.6 Hz, J=7.2 Hz), 3.85 (dd, 1H, J=9.1 Hz, J=5.3 Hz), 3.81-3.74 (m, 3H), 3.53 (dt, 1H, J=10.0 Hz, J=6.6 Hz), 3.47 (t, 1H, J=6.3 Hz), 2.90 (bd, 1H, J=2.1 Hz), 2.40 (dq, 1H, J=12.4 Hz, J=7.4 Hz), 2.20 (dq, 1H, J=12.4 Hz, J=7.4 Hz), 1.12-1.05 (m, 42H), 0.90 (s, 9H), 0.24 (s, 3H), 0.19 (s, 3H); LRMS for C$_{45}$H$_{83}$NO$_{12}$S$_2$Si$_3$ [M+Na]$^+$. found: 1000.7. calcd: 1000.5; [M−H]$^+$. found: 976.7. calcd: 976.5.

Synthesis of Gb5 Pentasaccharide 15

A mixture of thioglycoside 12 (373 mg, 0.38 mmol) and acceptor 13 (502 mg, 0.363 mmol) was azeotroped three times with anhydrous benzene and placed under high vacuum for 1 h. Freshly activated 4 Å MS (1.0 g) was added to the mixture, and that was taken up in dry CH$_2$Cl$_2$ (3.3 mL) and dry ether (6.6 mL), stirred for 5 min at RT, and cooled to 0° C. The mixture was stirred for 5 min at 0° C. and MeOTf (100 μL) was added dropwise. After the reaction was stirred for 2 h at 0° C., another portion MeOTf (116 μL) was added dropwise at 0° C. The reaction mixture was slowly warmed to RT for two days. Solid NaHCO$_3$ (0.5 g) was added and the reaction mixture was filtered through a Celite pad and concentrated. Purification by flash column chromatography using 9:1-6:1-4:1 hexane/EtOAc afforded a mixture of 13 and 14 as a white foam. The mixture 13 and 14 was dissolved in MeOH (5 mL), and NaOMe (0.1 mL, 25% in MeOH) was added to reach the pH=10, and the mixture was stirred at RT overnight. Concentration and purification by flash column chromatography using 6:1-4:1-2:1 hexane/EtOAc afforded 15 (486 mg, 55%). $^1$H NMR (500 MHz, CDCl$_3$) δ7.79 (d, 2H, J=7.5 Hz), 7.34-7.03 (m, 46H), 6.98 (d, 2H, J=7.0 Hz), 5.83-5.75 (m, 1H), 5.09 (d, 1H, J=3.2 Hz), 5.05-4.93 (m, 3H), 4.88-4.84 (m, 2H), 4.79-4.73 (m, 3H), 4.62-4.55 (m, 2H), 4.53-4.42 (m, 5H), 4.38-4.36 (m, 1H), 4.32-4.28 (m, 3H), 4.18-4.04 (m, 9H), 3.95 (d, 1H, J=2.1 Hz), 3.92-3.77 (m, 8H), 3.71-3.66 (m, 4H), 3.62-3.49 (m, 7H), 3.46-3.41 (m, 2H), 3.31-3.21 (m, 5H), 2.72 (t, 1H, J=5.7 Hz), 2.67 (dd, 1H, J=10.4 Hz, J=3.2 Hz), 2.59 (bs, 1H), 2.42 (d, 1H, J=3.1 Hz), 2.14-2.07 (m, 2H), 1.73-1.64 (m, 2H), 1.08-1.04 (m, 36H), 0.90 (s, 3H), 0.15 (s, 3H), 0.11 (s, 3H). LRMS for C$_{128}$H$_{173}$NO$_{27}$SSi$_3$ [M+Na]$^+$. found: 2295.0. calcd: 2295.1.

Synthesis of Gb5 Pentasaccharide 16

A solution of 15 (500 mg, 0.22 mmol) in dry THF (20 mL) was added TBAF (2.2 mL, 1.0 M in THF) at RT. The mixture was stirred at RT overnight. Concentration and purification by flash column chromatography using 1%-2%-4% MeOH/DCM afforded 6 (352 mg, 86.7%). $^1$H NMR (500 MHz, CDCl$_3$) δ7.82 (d, 2H, J=7.6 Hz), 7.33-7.05 (m, 46H), 6.92 (d, 2H, J=7.2 Hz), 5.82-5.77 (m, 1H), 5.07 (d, 1H, J=3.0 Hz), 5.02-4.73 (m, 8H), 4.64-4.61 (d, 1H, J=10.8 Hz), 4.57-4.53 (m, 2H), 4.51-4.48 (m, 2H), 4.46-4.44 (m, 2H), 4.40-4.37 (m, 1H), 4.34-4.31 (m, 2H), 4.23 (d, 1H, J=8.4 Hz), 4.20-4.13 (m, 4H), 4.08-4.04 (m, 4H), 3.95-3.73 (m, 11H), 3.69-3.64 (m, 6H), 3.62-3.48 (m, 9H), 3.43-3.40 (m, 2H), 3.34-3.30 (m, 2H), 3.25-3.18 (m, 4H), 3.02 (bs, 1H), 2.86 (bs, 2H), 2.74 (dd, 1H, J=10.2 Hz, J=2.7 Hz), 2.66 (bs, 1H), 2.62 (t, 1H, J=5.6 Hz), 2.14-2.12 (m, 2H), 1.76-1.61 (m, 18H), 1.40-1.35 (m, 2H). LRMS for C$_{104}$H$_{119}$NO$_{27}$SSi$_3$ [M+Na]$^+$. found: 1869.1. calcd: 1868.1.

Synthesis of GB5 Pentasaccharide 17

Na (350 mg, 15.2 mmol) was added to liquid NH$_3$ (30 mL) at −78° C., the mixture was stirred for 2 min under Ar to form a blue solution, and compound 16 (400 mg, 0.217 mmol) in THF (2 mL) was added to the blue solution. The mixture was stirred at −78° C. for 1 h and quenched by solid NH$_4$Cl (1.0 g). The ammonia was removed by a stream of Ar. To the solid was added pyridine (15 mL), acetic anhydride (10 mL) and a crystalline DMAP. The mixture was stirred at RT for two days. Concentration and purification by flash column chromatography using 1%-4%-10% MeOH/DCM afforded 17 (300 mg, 88%). $^1$H NMR (500 MHz, CDCl$_3$) δ 5.82-5.76 (m, 1H), 5.68 (d, 1H, J=5.7 Hz), 5.59 (d, 1H, J=2.8 Hz), 5.42 (d, 1H, J=3.0 Hz), 5.34 (d, 1H, J=3.1 Hz), 5.21-5.09 (m, % H), 5.03 (d, 1H, J=1.0 Hz), 4.99-4.95 (m, 2H), 4.92 (d, 1H, J=3.6 Hz), 4.89 (t, 1H, J=8.1 Hz), 4.75 (dd, 1H, J=10.9 Hz, J=2.5 Hz), 4.67 (dd, 1H, J=10.9 Hz, J=3.4 Hz), 4.61 (d, 1H, J=7.8 Hz), 4.53 (d, 1H, J=7.7 Hz), 4.46 (d, 1H, J=8.0 Hz), 4.44 (dd, 1H, J=10.8 Hz, J=1.5 Hz), 4.41 (dd, 1H, J=10.9 Hz, J=6.2 Hz), 4.36 (t, 1H, J=6.3 Hz), 4.22-4.18 (m, 2H), 4.17-4.03 (m, 7H), 4.00 (d, 1H, J=1.0 Hz), 3.93 (t, 1H, J=6.1 Hz), 3.89-3.82 (m, 2H), 3.80-3.75 (m, 2H), 3.62-3.59 (m, 2H), 3.51-3.44 (m 1H), 3.27 (m, 3.23 (m, 1H), 2.14, 2.12, 2.11, 2.10, 2.10, 2.087, 2.086, 2.08, 2.07, 2.06, 2.056, 2.056, 2.056, 2.04, 1.97, 1.93 (16 s, 48H), 1.70-1.62 (m, 2H). $^{13}$C NMR (125 MHz, CDCl$_3$) δ 170.89, 170.45, 170.45, 170.34, 170.30, 170.24, 170.21, 170.11, 170.01, 169.79, 169.66, 169.31, 169.31, 169.28, 168.94, 168.69, 137.59, 114.91, 100.67, 100.42, 100.35, 99.27, 98.93, 76.55, 76.31, 74.24, 72.60, 72.53, 72.36, 72.26, 71.80, 71.47, 71.09, 70.72, 70.47, 70.35, 69.88, 69.51, 69.12, 69.01, 68.90, 68.43, 67.50, 66.77, 62.11, 61.48, 61.24, 61.00, 60.13, 54.96, 53.56, 29.60, 28.36, 23.30, 20.78, 20.71, 20.68, 20.59, 20.57, 20.55, 20.51, 20.51, 20.51, 20.47, 20.44, 20.44, 20.38, 20.30, 20.25, 13.98, 13.87. LRMS for C$_{67}$H$_{93}$NO$_{41}$ [M+Na]$^+$. found: 1590.6. calcd: 1590.5.

Synthesis of Gb5 Glycoamino Acid 10

To a solution of 17 (200 mg, 0.128 mmol) and allyl glycine (450 mg, 1.05 mmol) in DCM (4 mL) was added Hoveyda Grubbs I catalyst (36 mg, 0.06 mmol). The mixture stirred at 35° C. for two days. Concentration and purification by flash column chromatography using 10:1-3:1-1:3

Hexane/EtOAc and followed by 10% MeOH/DCM afforded a mixture of product and starting material 7 (190 mg). The crude product was dissolved in MeOH/water (10:1, 10 mL), and Pt(C) 56 mg was added, connected to cylinder of $H_2$ at pressure 1 atm, and the mixture was stirred at RT overnight. The reaction mixture was filtered through Celite, the filtrate was evaporated and the residue loaded onto flash chromatography column, eluting with 7% MeOH/DCM containing 0.3% HOAc. Product 10 was collected. The product was reloaded on PTLC and eluted with AcOH-MeOH—$CH_2Cl_2$ (0.3:7:100). Gb5 glycoamino acid 10 was collected (120 mg, yield 51%). $^1$H NMR (500 MHz, MeOD) δ 7.81 (d, 2H, J=7.6 Hz), 7.68 (t, 2H, J=7.1 Hz), 7.40 (t, 2H, J=7.4 Hz), 7.31 (t, 2H, J=7.4 Hz), 5.65 (d, 1H, J=2.8 Hz), 5.34 (d, 1H, J=3.2 Hz), 5.32 (d, 1H, J=2.8 Hz) 5.19-5.15 (m, 2H), 5.10-4.93 (m, 5H), 4.81 (t, 1H, J=8.3 Hz), 4.70-4.67 (m, 2H), 4.57 (d, 1H, J=8.0 Hz), 4.48-4.36 (m, 5H), 4.25-3.94 (m, 17H), 3.83-3.75 (m, 3H), 3.70-3.67 (m, 1H), 3.52-3.47 (m, 1H), 2.15, 2.12, 2.11, 2.107, 2.10, 2.09, 2.08, 2.07, 2.034, 2.024, 2.033, 2.033, 2.02, 1.99, 1.94, 1.92, 1.84-1.80 (m, 1H), 1.68-1.66 (m, 1H), 1.57-1.54 (m, 2H), $^{13}$C NMR (125 MHz, CDCl$_3$) δ 171.98, 170.66, 170.60, 170.57, 170.46, 170.42, 170.36, 170.24, 170.14, 170.06, 170.00, 169.63, 169.56, 169.41, 169.30, 168.90, 256.67, 101.06, 100.49, 100.17, 99.35, 98.74, 79.41, 76.06, 74.39, 72.89, 72.65, 72.43, 70.05, 71.89, 71.78, 71.20, 70.96, 70.75, 70.14, 70.03, 69.97, 69.20, 68.94, 67.97, 67.68, 66.74, 62.20, 62.12, 61.15, 61.10, 60.89, 36.94, 35.80, 32.57, 30.00, 29.22, 28.89, 28.38, 25.57, 25.33, 23.59, 23.22, 20.96, 20.93, 20.93, 20.88, 20.80, 20.80, 20.80, 20.77, 20.77, 20.77, 20.77, 20.69, 20.68, 20.65, 20.54, 20.50. LRMS for $C_{85}H_{110}N_2O_{45}$ [M+Na]$^+$. found: 1901.7. calcd: 1901.6.

Example 4

Synthesis of Gb5 Conjugates for ELISA Assays

Synthesis of Gb5-Lipid 4-4

4-4

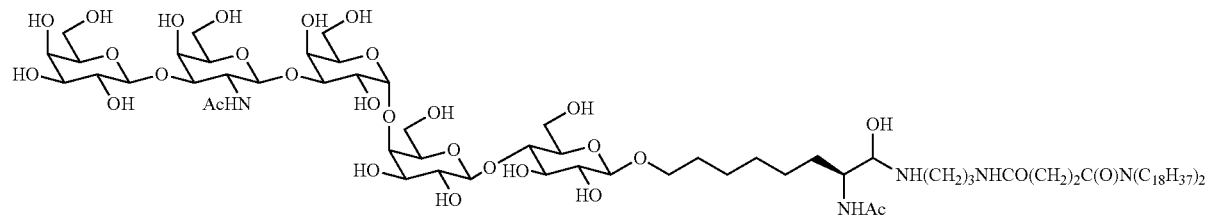

Figure 3:
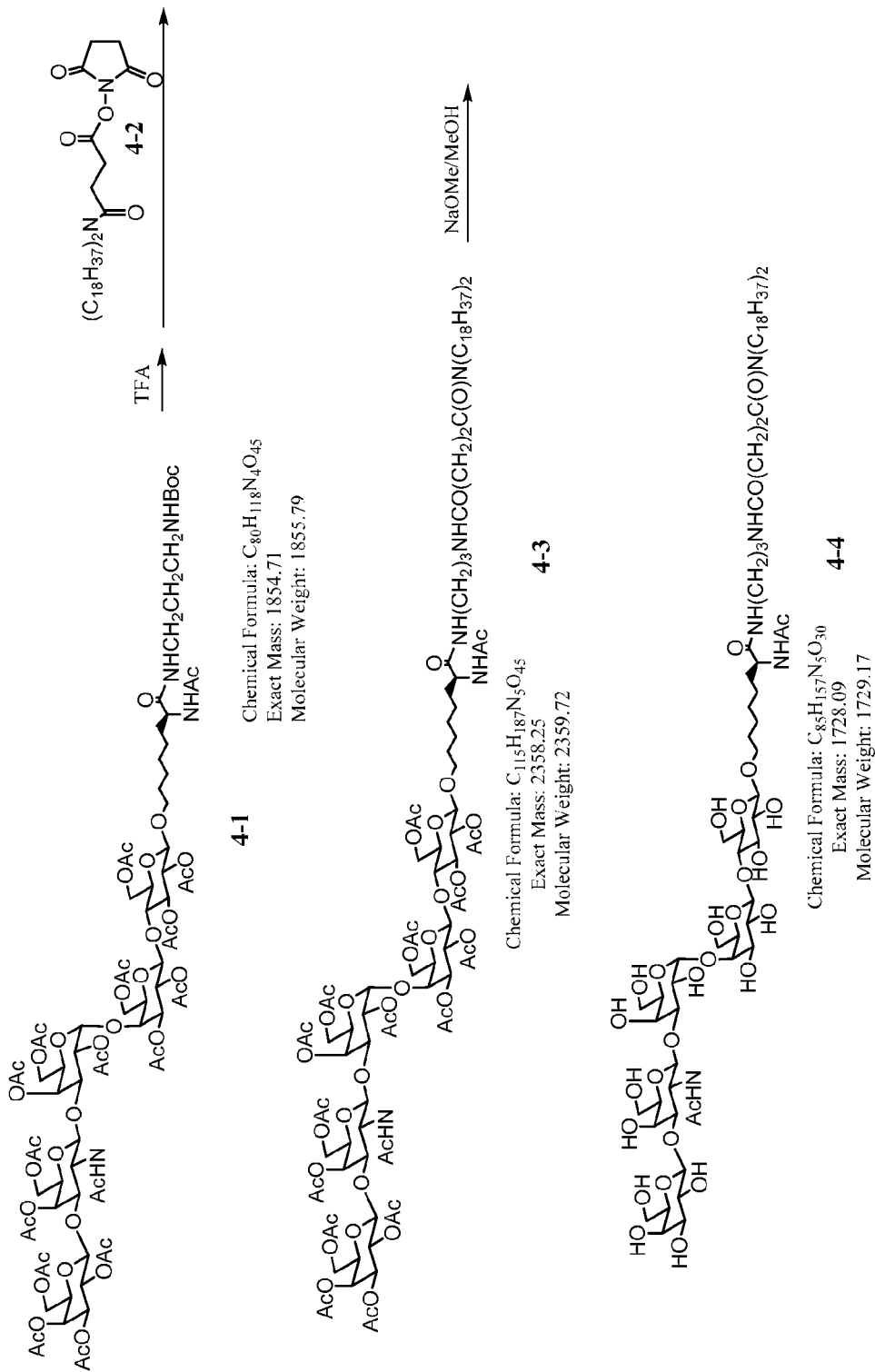
FIG. 3 depicts a synthetic scheme of Gb5-lipid compound 4-4.
Figure 4A:
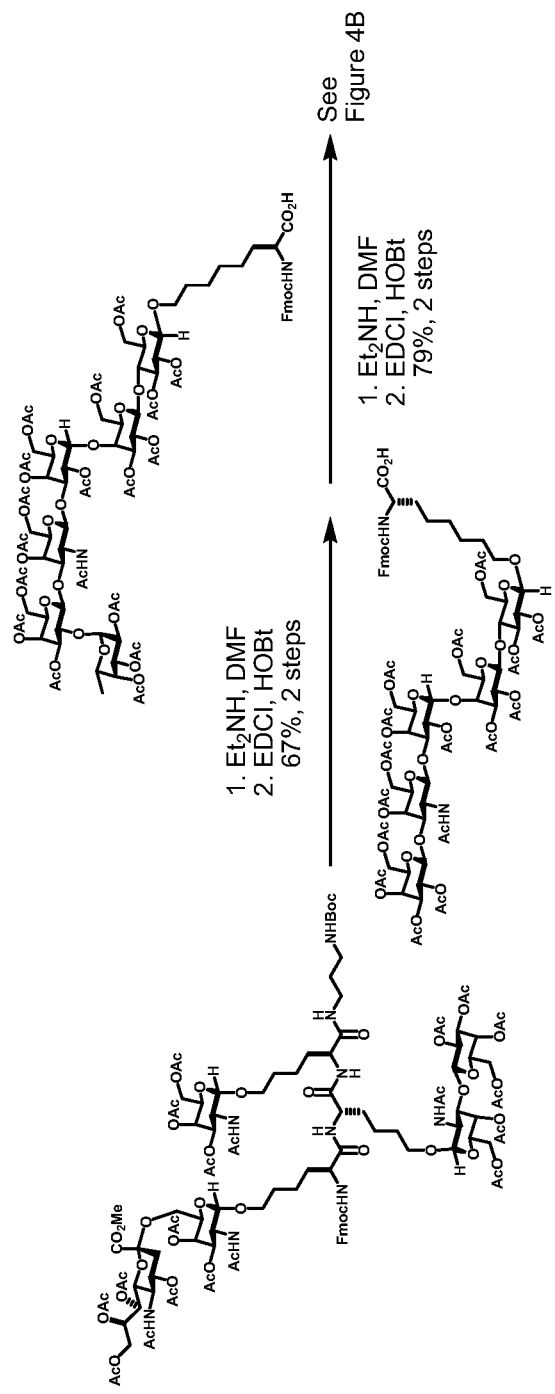
FIGS. 4A-C depict a synthetic scheme for the synthesis of pentavalent GloboH-Gb5-STn-TF-Tn compounds.
Figure 4B:
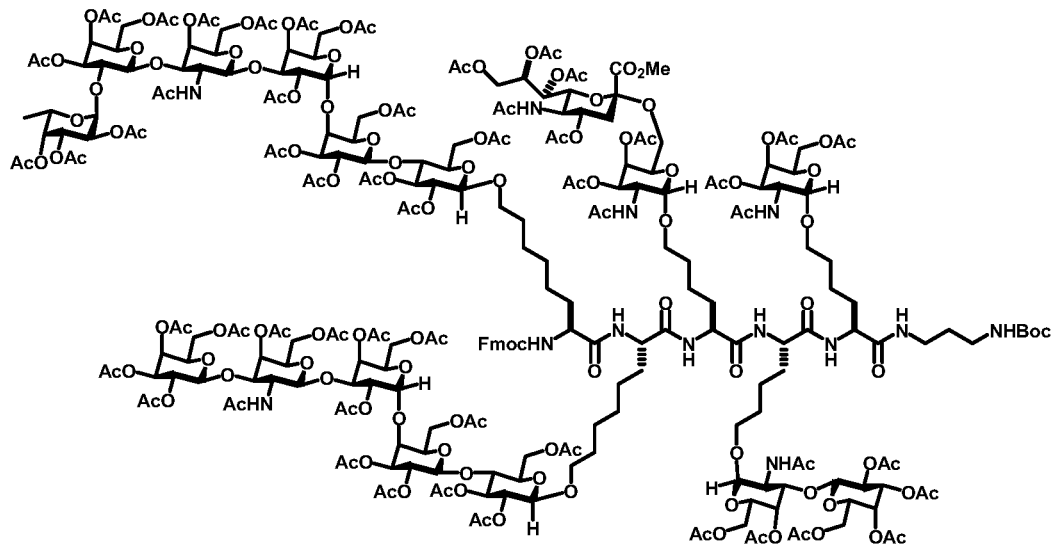
Figure 4B:
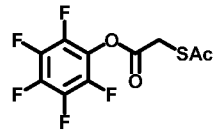
Figure 4C:
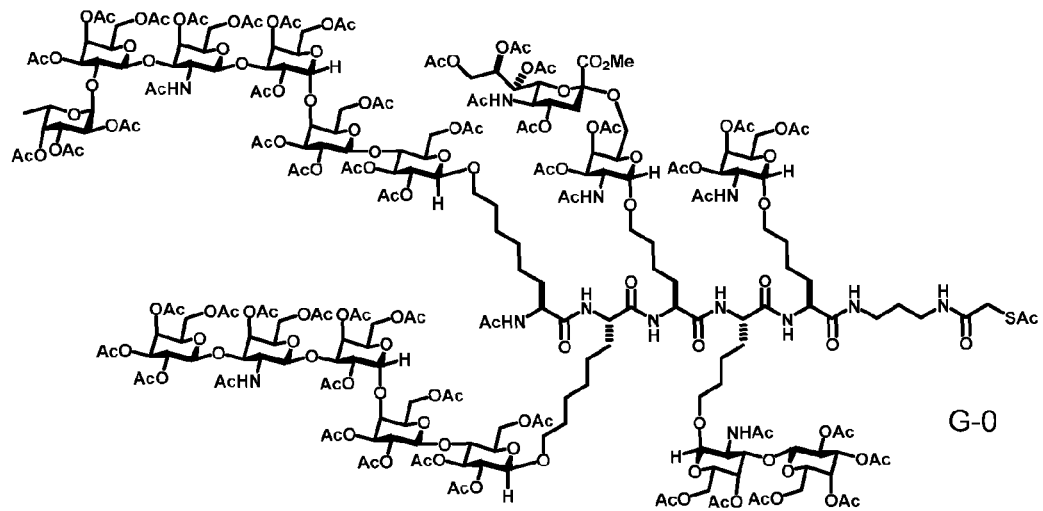
Figure 4C:
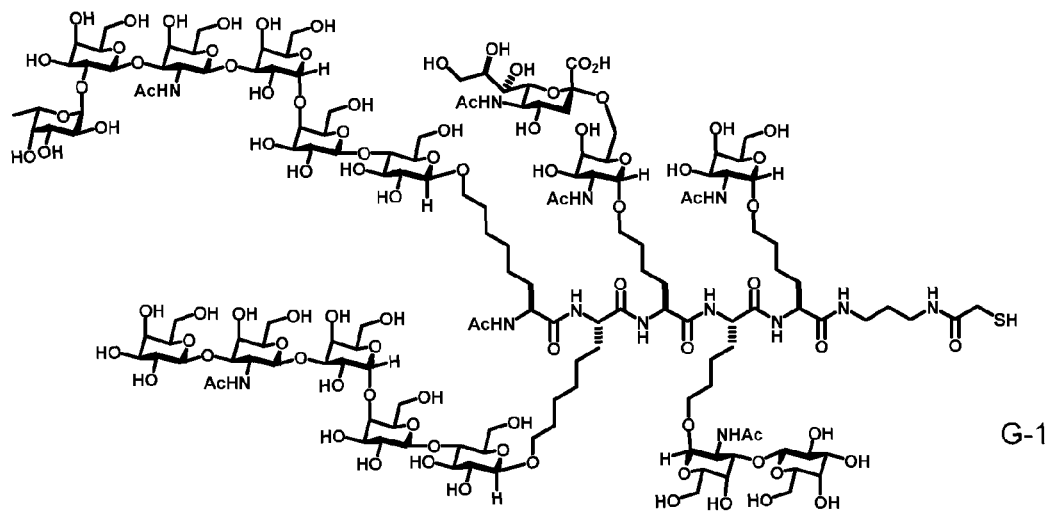
Figure 5:
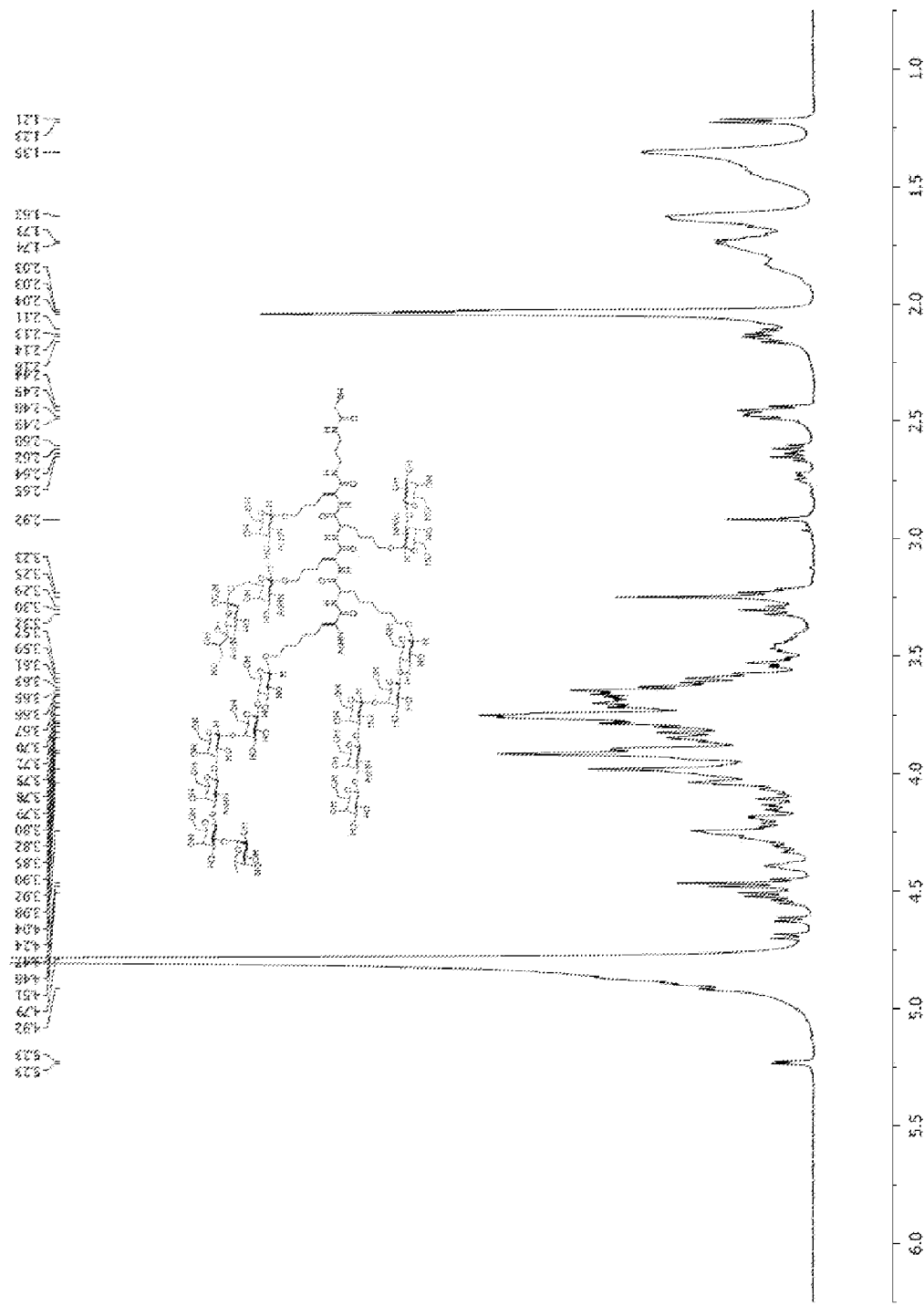
FIG. 5 is a $^1$H NMR spectrum of pentavalent GloboH-Gb5-STn-TF-Tn compound G-1.

As shown in FIG. 3, a solution of 4-1 (13 mg, 7.0 μmol) in DCM/TFA (⅓, 0.6 mL) was stirred at RT for 30 min. The solvent was removed and the residue was taken directly into the next step without purification. The residue was dissolved in DCM (1.0 mL), and compound 4-2 (30 mg, 41.7 mol) (Schmitt, L.; Dietrich, C.; Tampe, R. *J. Am. Chem. Soc.* 1994, 116, 8485-8491) and DIPEA (50 μL) were added to the mixture. The reaction was stirred at RT overnight. Concentration and purification by flash column chromatography using 1%-5% MeOH/DCM afforded 4-3 (14 mg, 85%).

To a solution of 4-3 (12 mg, 5.1 μmol) in MeOH (1.0 mL) was added NaOMe (25% NaOMe/MeOH, 12 μL), and the mixture was stirred at RT for 2 h. The reaction was quenched with 1 N HCl to a final pH of 6.5-7.0. The solvent was removed and the residue was dissolved in $H_2O$ (1.0 mL). The product 4-4 (8 mg, 91%) was obtained after lyophilization. MS (m/z): 865.2 [M+2H]$^+$, 1730.2 [M+H]$^+$ Synthesis of Gb5-KLH 4-5

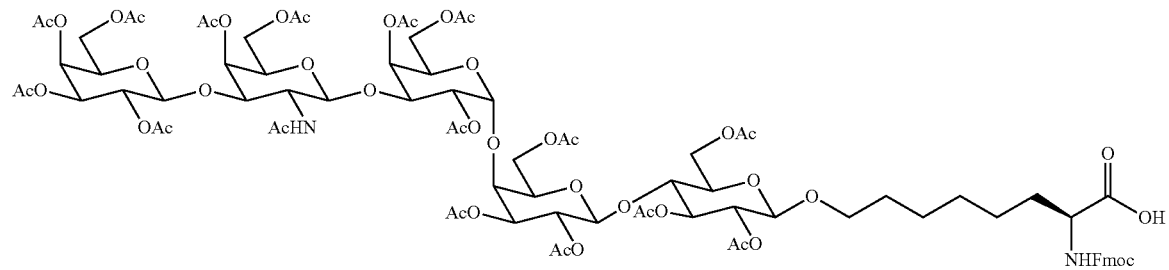

4-6

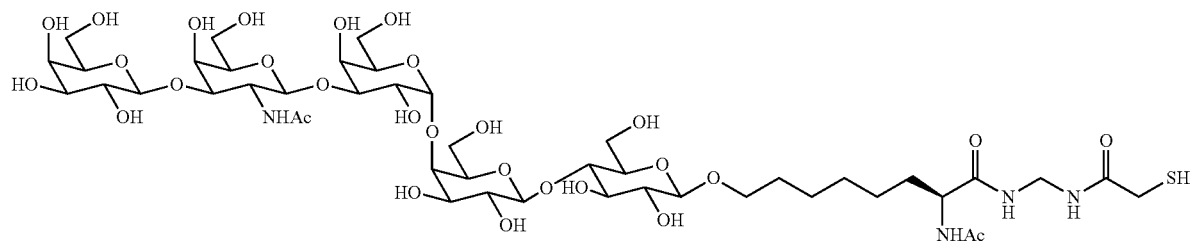

Procedure: 20 mg of chlorotrityl resin (0.02 mmol) was treated with mercaptoacetic acid (50 uL+950 uL methylene chloride) for one hour, then washed 3× with DMF. The resin was then activated with PyBOP (21 mg, 0.04 mmol) and DIEA (16 mg, 21 uL, 0.12 mmol) for 10 minutes in DMF, followed by the addition of 1,3-diaminopropane (15 mg, 0.2 mmol). After 20 minutes, the resin was washed 3× with DMF. 10 mg of 4-5 (0.0054 mmol) was dissolved in 200 uL of DMF and added to the resin. PyBOP (8 mg, 0.015 mmol) and DIEA (7.42 mg, 10 uL, 0.057 mmol) in 150 uL DMF were added and mixed for two hours. The resin was washed 3× with DMF. Two washes with 30% piperidine in DMF for 10 minutes were performed, followed by washes with DMF (3×). The resin was treated with 20 uL of acetic anhydride in 500 uL DMF for 30 minutes, then washed with DMF (3×). Several washes with methylene chloride were performed. The protected carbohydrate was then cleaved from resin by treatment with 50% TFA in DCM for 10 minutes, and evaporated. The oil was resuspended in 50% acetonitrile in water, frozen and lyophilized overnight, resulting in a white powder. The powder was treated with a solution of 0.3 N NaOH for two hours, neutralized with HCl, and purified by reverse phase HPLC (C18). The compound 4-6 was obtained as a white powder. MS of 4-6 (m/z)=1199.1 (M+H$^+$).

To prepare the Gb5-KLH conjugate described in Example 5, compound 4-6 was conjugated to KLH using the procedure described in Example 1.

Example 5

This Example describes immunogenic studies performed with mice immunized with a Gb5-KLH conjugate prepared in Example 4. Unless otherwise indicated below, the protocols described in Example 2 were followed.

While not wishing to be bound by any particular theory, it appears that the IgG values for boost-vaccination serum may be higher than shown in Table 3. During the initial data collection, the concentration of IgG in this experiment was much higher than expected, and further serial dilutions would likely result in defined IgG titer values higher than those shown in Table 3.

TABLE 3

Antibody titers by Enzyme-Linked ImmunoSorbent Assay (ELISA)[a] Gb5-KLH (5 ug) + OPT-821 adjuvant (QS-21 analog) (20 ug)

| | Gb5-lipid | | | |
|---|---|---|---|---|
| | Post-Vaccination | | Boost-Vaccination | |
| Mouse # | IgM | IgG | IgM | IgG |
| Pre-serum | 0 | 0 | 0 | 0 |
| 1 | 0 | 640 | 0 | 2560 |
| 2 | 0 | 1280 | 20 | >2560 |
| 3 | 0 | 320 | 20 | >2560 |
| 4 | 0 | 640 | 0 | >2560 |
| 5 | 0 | 640 | 80 | >2560 |
| Median | 0 | 640 | 20 | >2560 |

[a]IgM or IgG antibody reciprocal titers of pre- and post-vaccination sera tested for the antigen in the monovalent Gb5-KLH vaccine. ELISA assays were performed to determine IgM or IgG serum antibody titers as previously described (Ragupathi 2002 & 2003, supra). In brief, Gb5-lipid was coated on ELISA plates at an antigen dose of 0.1 μg/well and incubated overnight at 4° C.. Nonspecific sites were blocked with 1% human serum albumin (HSA) for 2 h, and serially diluted antiserum was added to each well. After 1 h of incubation, the plates were washed, and alkaline phosphatase labeled goat anti-mouse IgM or IgG was added at 1:400 dilution (Southern Biotechnology Associates, Inc., Birmingham, AL). The antibody titer was defined as the highest dilution with absorbance of 0.1 or greater over that of normal control mouse sera.

Example 6

Synthesis of a Unimolecular Pentavalent Vaccine Construct Containing Globo-H, Gb5, STn, TF and Tn. (See FIG. 4.)

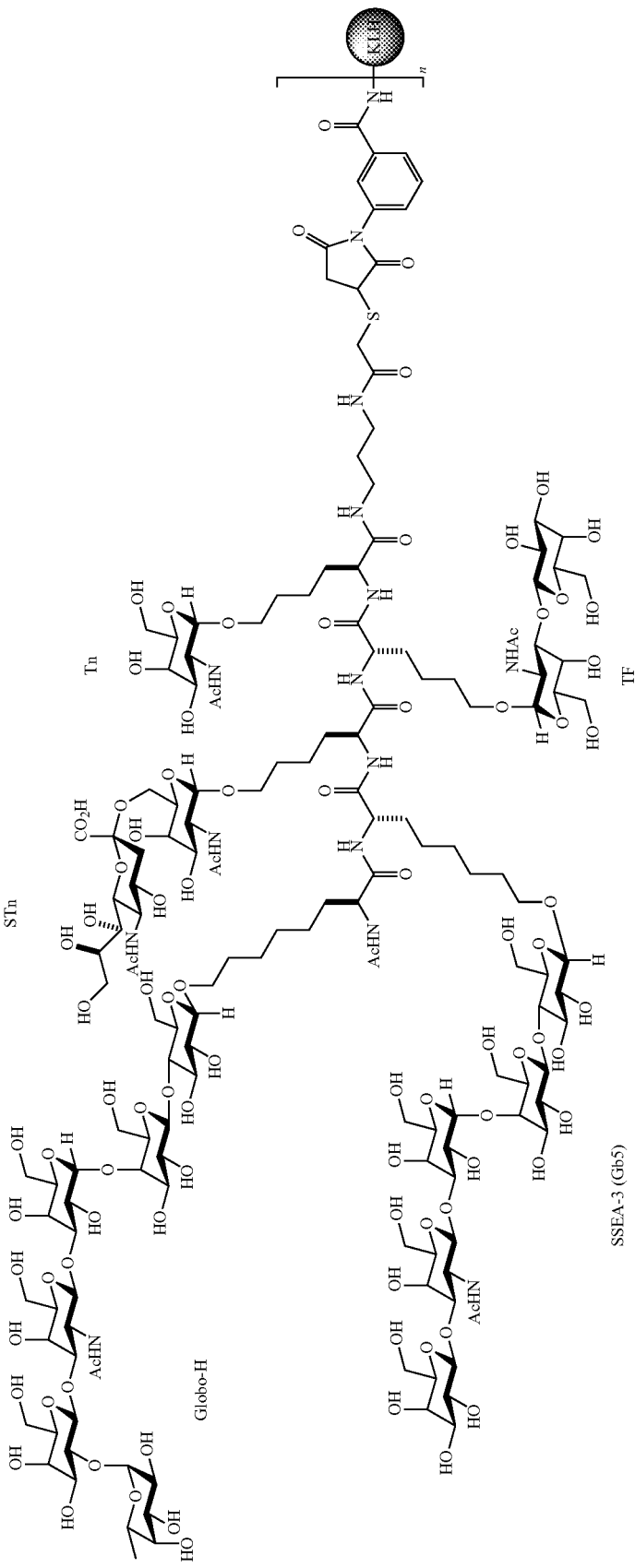

This Example describes the preparation of the conjugate G-2. The procedure for synthesizing and conjugating this construct is substantially the same as described for the conjugate in Example 1 (Keding, S. J.; Danishefsky, S. J. Proc. Natl. Acad. Sci. USA 2004, 101, 11937-11942; Ragupathi, G.; Koide, F.; Livingston, P. O.; Cho, Y. S.; Endo, A.; Wan, Q.; Spassova, M. K.; Keding, S. J.; Allen, J.; Ouerfelli, O.; Wilson, R. M.; Danishefsky, S. J. J. Am. Chem. Soc. 2006, 128, 2715-2725), except that the Gb5 glycosyl amino acid was substituted for the GM2 glycosyl amino acid in the synthesis of AcHN-GloboH-Gb5-STn-TF-Tn-CONH—$(CH_2)_3$—NHCOCH$_2$SAc (G-0). See FIG. 4 for a scheme of the fully deprotected unimolecular pentavalent construct containing Globo-H, Gb5, STn, TF, and Tn.

Synthesis of AcHN-GloboH-Gb5-STn-TF-Tn-CONH—$(CH_2)_3$—NHCOCH$_2$SH (G-1)

To a round-bottom flask containing peracetylated AcHN-GloboH-Gb5-STn-TF-Tn-CONH—$(CH_2)_3$—NHCOCH$_2$SAc (G-0) (11.8 mg, 2.02 µmol) was added 1.2 mL of degassed 2:1 MeOH/0.3 M aqueous NaOH. The resulting clear, colorless solution was stirred at room temperature under Ar atmosphere for 24 hours, then an additional 1.2 mL of degassed 0.3 M aqueous NaOH was added. After stirring for another 40 hours, the reaction mixture was neutralized by dropwise addition of acetic acid (27 µL, 0.472 mmol) and then concentrated by rotary evaporation. The resulting solution was treated with TCEP (50 µL, 0.025 mmol) at room temperature for 2 hours, then purified on a Bio-Gel P-4 column (1.5×17 cm) with water as the eluent. Fractions containing the desired product were combined and lyophilized to give G-1 as a white powder in 92% yield (7.1 mg, 1.87 µmol). MS (ESI+) m/z 1290.93 $[M+3Na]^{3+}$.

Conjugation of Unimolecular Pentavalent Vaccine Construct Containing Globo-H, Gb5, STn, TF and Tn (G-2).

Carrier protein KLH was first incubated with sulfo-MBS (m-maleimidobenzoyl-N-hydroxysuccinimide) in pH 7.4 phosphate buffer containing 0.9 M sodium chloride for 1 hour and 45 minutes. Next, the unconjugated sulfo-MBS was eliminated by passage over a G25 Sephadex column (PD MiniTrap G-25; GE Healthcare) and maleimide-activated KLH was then obtained. Glycopeptide construct G-1 (freshly prepared, passed through TCEP gel immediately prior to use) was mixed with freshly prepared maleimide-activated KLH in pH 7.4 phosphate buffer containing 0.9 M sodium chloride and 100 mM EDTA and stirred at room temperature for 4 hours. Following incubation, unreacted glycopeptide was removed using an Amicon Ultra-4 centrifugal filter unit (50,000 molecular weight cut off; Millipore). Finally the corresponding KLH conjugate G-2 was obtained as a phosphate buffer solution.

The number of copies of glycopeptide construct incorporated in the KLH conjugate was determined to be 593 per KLH by hydrolytic carbohydrate analysis and standard protein analysis (Bio-Rad dye-binding method).

Example 7

This Example describes, among other things, studies to measure toxicity following immunization with the pentavalent construct described in Examples 1 and 2, and determination of the lowest immunogenic dose among preselected vaccine dose levels that meet criteria for immunogenicity and safety. It will be appreciated that the methods and materials described in this Example may be extended to the pentavalent construct described in Example 5.

Ovarian cancers express a rich array of cell-surface antigens, including the carbohydrate epitopes GM2, Globo-H, Lewis, sialyl Tn (sTn), Tn, Thompson Friedreich antigen (TF) and mucin 1 (Muc1) (Federici M F, Kudryashov V, Saigo P E, et al. Int J Cancer 81:193-8, 1999; Zhang S, Cordon-Cardo C, Zhang H S, et al. Int J Cancer 73:42-9, 1997; Zhang S, Zhang H S, Cordon-Cardo C, et al. Clin Cancer Res 4:2669-76, 1998; Zhang S, Zhang H S, Cordon-Cardo C, et al. Int J Cancer 73:50-6, 1997). Various methods have been used to generate an immune response against such defined antigens. In previous work with monovalent antigens, investigators have achieved consistent immunogenicity by conjugating an antigen to keyhole limpet hemocyanin (KLH), an immunogenic carrier protein, with the immunological adjuvant, saponin QS-21 (Livingston P O, Zhang S, Lloyd K O. Cancer Immunol Immunother 45:1-9, 1997). Monovalent vaccination has resulted in immunologic responses (Livingston P O, Natoli E J, Calves M J, et al. Proc Natl Acad Sci USA 84:2911-5, 1987 Slovin S F, Ragupathi G, Fernandez C, et al. Vaccine 23:3114-22, 2005; Slovin S F, Ragupathi G, Adluri S, et al. Proc Natl Acad Sci USA 96:5710-5715, 1999; Sabbatini P J, Kudryashov V, Ragupathi F, et al. Int J Cancer 87:79-85, 2000). However, tumor cell surface antigens display marked heterogeneity and the multivalent approach to generate a broader immune response is attractive.

Applicant recently characterized the safety and immunogenicity of an individually constructed multivalent antigen-KLH plus QS 21 vaccine construct in patients with epithelial ovarian, fallopian tube or peritoneal cancer in $2^{nd}$+complete clinical remission (Sabbatini P J, Ragupathi G, Hood C, et al. Clin Ca Res 13(14):4170-7, 2007). Eleven patients in this pilot trial received a multivalent vaccine subcutaneously containing GM2 (10 µg), Globo-H (10 µg), LeY (10 µg), Tn(c) (3 µg), STn(c) (3 µg), TF(c) (3 µg), Tn-MUCl (3 µg) individually conjugated to KLH and mixed with adjuvant QS21(100 µg). Vaccinations were administered at weeks 1, 2, 3, 7, and 15. Periodic blood and urine samples were obtained to monitor safety (CBC, comprehensive panel, amylase, TSH, urinalysis) and antibody production (ELISA, FACS, CDC). All 11 patients were included in the safety analysis; 9/11 remained on study for at least 2 weeks past 4th vaccination and were included in the immunologic analysis (2 withdrew, disease progression). The vaccine was well tolerated. Self-limited and mild fatigue (maximum grade II in 2 patients), fever, myalgia, and localized injections site reactions were most frequent. No clinically relevant hematologic abnormalities were noted. No clinical or laboratory evidence of autoimmunity was seen. Serologic responses by ELISA were largely IgM against each antigen with the exception of Tn-MUC 1 where both IgM and IgG responses were induced. Antibody responses were generally undetectable prior to immunization. After immunization, median IgM titers were as follows: Tn-MUC 1 1:640 (IgG 1:80), Tn 1:160, TF 1:640, Globo-H 1:40, and STn 1:80. Only 1 response was seen against Lewis-Y; 2 against GM2. 8/9 patients developed responses against at least 3 antigens. Antibody titers peaked weeks 4-8 in all patients. FACS and CDC analysis showed substantially increased reactivity against MCF7 cells in 7/9 patients, with some increase seen in all patients. Applicant concluded that the multivalent-KLH conjugate plus QS21 vaccine safely induced antibody responses against 5 of 7 antigens and conclude that an adequately powered efficacy trial is the next step to determine if a clinical benefit from vaccination would be present.

Based on the available immunogenicity and safety data, a phase III randomized, double-blind trial (n=164 patients)

will be conducted to evaluate the individually constructed multivalent vaccine containing the antigens, GM2, Globo-H, Tn-Mucl, and TF, each individually conjugated to KLH, with an immunologic adjuvant versus adjuvant alone. Applicant is manufacturing the vaccine, and will serve as the lead center for the study. Regulatory requirements require validation of each individual component of the vaccine mixture (which was done over a period of sequential phase I trials), increased amounts of carrier proteins are required (a fixed amount for each individual component), and the synthesis of each monovalent-KLH construct involves a low yielding final conjugation step. The unimolecular construct proposed in this Example greatly simplifies manufacture, and provides easy scalability.

A unimolecular pentavalent vaccine, bearing the antigens Globo-H, sTn, Tn, Lewis$^y$ and TF, conjugated to KLH and with QS-21 as an adjuvant, was recently synthesized and studied in a preclinical setting (see Example 2) (Ragupathi G, Koide F, Livingston P O, et al. J Am Chem Soc 128: 2715-25, 2006). Mice were immunized, and immunologic responses were seen with the exception of the Lewis antigen. (The difficulty demonstrating immunogenicity with the Lewis antigen was also previously seen in the monovalent phase I study.) The ELISA and FACS data shown in Example 2 suggest that the immunological properties of the antigens were preserved and supports the concept of considering unimolecular multi antigenic synthetic vaccines. The present Example describes human evaluations in a phase I trial setting.

For the phase I study, a unimolecular multivalent vaccine is prepared as described in Example 1, bearing the antigens, Globo-H, GM2, sTn, TF and Tn, conjugated to KLH and mixed with QS-21.

Conjugation

Antigen-KLH ratios were expected to range between 80:1 and 1200:1, assuming a KLH molecular weight of $8.6 \times 10^6$. SDS-Page Gels were performed and Western blot analysis conducted with each lot of antigen-KLH for comparison to future lots. Sterility and safety testing was performed with vialed product. Toxicity testing was performed at greater than 50 times the dose/meter$^2$ to be used in clinical trial. No growth in culture and no adverse reaction in mice (including weight loss of 10% or more) were allowed. Three or more mice were immunized on 3-4 occasions at 1-2 week intervals, with post immunization sera testing. Antibody titers of 1:40 or greater against at least four antigens and FACS staining of greater then 25% of antigen positive cells were required to confirm appropriate immunogenicity.

Adjuvant

QS-21 is an immunological adjuvant obtained from Antigenics Incorporation. It was mixed with the multivalent antigen conjugate at the time of vaccine vialing. The dose of QS-21 is 100 mcg. The final pentavalent antigen-KLH plus QS-21 adjuvant were combined, sterile filtered, and vialed. The product was then tested for sterility, endotoxin, immunogenicity, and safety. The vaccine vials are stored at −70 to −80 degrees Celsius.

The study investigates the safety and immune responses following immunization with the unimolecular pentavalent Globo-H-GM2-sTn-TF-Tn-KLH conjugate, plus the immunological adjuvant QS-21. This is a phase I study to assess toxicity and immunogenicity. Approximately 24 patients with epithelial ovarian, fallopian tube and peritoneal cancer are vaccinated.

The injection is administered subcutaneously during weeks 1, 2, 3, 7 and 19, totaling five injections over the course of the study. Three dose levels are planned: 25 mcg, 50 mcg and 10 or 100 mcg; six patients are vaccinated at each dose level unless 2 dose limiting toxicities are observed, and an expansion cohort of 6 patients are enrolled at the lowest immunogenic dose level successfully enrolled.

Criteria for Subject Eligibility

Subject Inclusion Criteria:

1. Histologically documented stage III or IV epithelial carcinoma arising in the ovary, fallopian tube or peritoneum at diagnosis with one of the following high-risk attributes: a) clear cell or mucinous features or histology, b) suboptimal debulking, or c) failure to normalize the CA-125 by third cycle of primary chemotherapy 2. History of cytoreductive surgery and chemotherapy with at least one platinum-based chemotherapy regimen as part of primary treatment.

3. Patients must be in a first complete clinical remission. Complete clinical remission is defined as serum CA-125 within institutional normal limits, negative physical examination, and no definite evidence of disease by computed tomography (CT) of the abdomen and pelvis. Lymph nodes and/or soft tissue abnormalities ≤1.0 cm are often present in the pelvis and will not be considered definite evidence of disease. Eligibility is determined by anatomical imaging only (ie. MRI or CT). Positive PET image (if performed) does not exclude a patient if other criteria are met and anatomical imaging is negative.

4. Adequate organ function defined by:
   a. Bone marrow function: Absolute neutrophil count (ANC) greater than or equal to 1,000/mm$^3$, equivalent to Common Toxicity Criteria (CTCAE v3.0) grade 1. Platelets greater than or equal to 100,000/mm$^3$
   b. Renal function: Serum creatinine less than or equal to 1.5× institutional upper limit normal (ULN), CTCAE v3.0 grade 1.
   c. Hepatic function: Bilirubin, SGOT, and alkaline phosphatase less than or equal to 2.5×ULN.

5. Stool guaiac is negative.

6. KPS>80%.

7. Age>18 years.

8. Patients must have recovered from clinically significant side effects from prior chemotherapy.

Subject Exclusion Criteria:

1. Pregnant or nursing women

2. Patients with other invasive malignancies who had (or have) any evidence of the other cancer present within the last 5 years, or whose previous cancer treatment contraindicated this protocol therapy are excluded. Non-melanoma skin cancers are an exception and will not exlude any patient.

3. Patients with a history of a seafood allergy.

4. Patients who have previously received a vaccine with any of the antigens in the current trial.

5. Patients with a history of immunodeficiency or autoimmune disease (excluding treated hypothyroidism).

6. Patients with active CNS tumor.

Pretreatment Evaluation

Within two weeks: pregnancy test for women of childbearing potential.

Within three weeks: complete history and physical examination; complete blood count with differential, comprehensive panel (AST, ALT, sodium, potassium, chloride, $CO_2$, calcium, glucose, total protein, albumin, alkaline phosphatase, creatinine, BUN, bilirubin); CA-125; thyroid stimulating hormone (TSH) level; urinalysis; stool hemoccult.

Within four weeks: CT scan of the abdomen and pelvis (with or without chest) or MRI; CXR (not required if CT imaged chest); standard pathology review.

Treatment/Intervention Plan

The unimolecular pentavalent vaccine is administered during weeks 1, 2, 3, 7 and 19. The vaccine is administered via subcutaneous injection in the outpatient clinic. Random sites on the upper arms or thighs are used. Three dose levels are used: 25 mcg, 50 mcg and either 10 mcg or 100 mcg depending on immunogenicity and safety of the first two dose levels. Six patients are injected at each dose level unless dose limiting toxicity is observed. An expansion cohort of six patients is enrolled at the the lowest immunogenic dose level successfully enrolled. Approximately 24 patients are accrued to the trial.

| Cohort | Treatment dose |
|---|---|
| I (# patients = 1-6) | 25 mcg |
| II (# patients = 1-6) | 50 mcg |
| III (# patients = 1-6) | 10 mcg or 100 mcg |

Expansion to 12 patients will occur at at the lowest immunogenic dose level successfully enrolled.

Progression to the next cohort or to the expansion cohort can proceed when no more than one out of 6 patients on a given cohort has received 4 of 5 planned vaccinations with no evidence of DLT.

Study treatment should be discontinued for Dose Limiting Toxicity (DLT). Patients are followed if study treatment is discontinued for toxicity. DLT is defined by:

a. Grade III allergic reaction. (Grade II is defined as rash, flushing, urticaria, dyspnea or drug fever >38 degrees Celsius; Grade III is defined as symptomatic bronchospasm, requiring parenteral medications, with or without urticaria, allergy related edema or angioedema; Grade IV is defined as anaphylaxis.)
b. Grade III autoimmune reaction (Grade II is defined as evidence of autoimmune reaction involving a non-essential organ or function (e.g. hypothyroidism) requiring treatment other than immunosuppressive drugs. Grade III is a reversible autoimmune reaction involving a major organ (e.g. colitis)
c. ≥Grade III hematologic or non-hematologic toxicity including fever. (Grade III fever is >40° C. for <24 hours).
d. Grade III injection site reaction. (Grade III is defined as ulceration or necrosis that is severe or prolonged, or requiring surgery).

Evaluation During Treatment/Intervention

| Week | Pre | 1 | 2 | 3 | 7 | 11 | 15 | 19 | 23 | Q3 mos. |
|---|---|---|---|---|---|---|---|---|---|---|
| Injection | | 1 | 2 | 3 | 4 | | | 5 | | |
| History & Physical | X | X | X | X | X | X | X | X | X | X |
| CMP | X | X | | X | X | X | X | X | X | X |
| CBC with differential | X | X | | X | X | X | X | X | X | X |
| CA-125 | X | | | | X | | X | | X | X |
| TSH | X | | | | | | | | X | |
| Urinalysis | X | | | | | | | | X | |
| Pathologic review | X | | | | | | | | | |
| Pregnancy test | X | | | | | | | | | |
| Stool hemoccult | X | | | | | | | | | |
| CT scan | X | | | | | X | | X | | X |
| Serology (3 Red Tops) | | | X | X | | X | X | X | X | X |
| Serology (6 Red Tops) | | X | | | X | | | | | |

Immununologic Response

The patients' sera is tested by ELISA for antibodies against each individual antigen in this vaccine. FACS analysis and complement dependent cell cytotoxicity are also evaluated with selected sera against a variety of cell lines expressing (or not) these particular antigens. Peripheral blood (60 mL) is drawn during weeks 1 and 7. Peripheral blood (30 mL) is drawn during weeks 2, 3, 11, 15, 19 and 23. Thereafter, blood is obtained every three months for as long as patient remains followed on study and is in remission.

Toxicities/Side Effects

The expected safety of the proposed vaccine is based on accumulating clinical experience with the multivalent monomeric vaccines utilizing the same antigens (albeit not using the unimolecular construct) in patients with a variety of malignancies, including ovarian cancer. Vaccination with the individual components has been well tolerated as previously described (Gilewski T, Ragupathi G, Bhuta S, et al. Proc Natl Acad Sci USA 98:3270-5, 2001; Helling F, Zhang S, Shang A, et al. Cancer Res 55:2783-8, 1995; Slovin S F, Ragupathi G, Musselli C, et al. Cancer Immunol Immunother 54:694-702, 2005; Slovin S F, Ragupathi G, Musselli C, et al. J Clin Oncol 21:4292-8, 2003). Toxicity is graded in accordance with the Common Toxicity Criteria Version 3.0 developed by the National Cancer Institute (NCI).

Criteria for Therapeutic Response/Outcome Assessment

The primary endpoints of this study are to describe immunogenicity, assess toxicity, and determine the lowest immunogenic dose across multiple dose levels. While not a primary endpoint, extent of disease is evaluated with history and physical exams, CA-125 determination, and imaging.

Antibodies against various antigens are studied by ELISA, and against human tumor cell lines by FACS when appropriate.

Patients are followed every three months if feasible following completion of the vaccine trial, until evidence of disease progression by CT imaging.

Efforts shall be made to account for all patients entered into the study during the evaluation or results. All patients are considered evaluable for safety and immune response.

Patients are in remission at the start of the study and are removed for radiographic evidence for disease progression or utilizing CA-125 criteria as below.

Patients who have disease progression before the 4th vaccination, and who are removed from study due to progression only (i.e. no toxicity otherwise defined as DLT) are replaced in order to have an adequate cohort to assess toxicity.

Criteria for Removal from Study

Therapy may be discontinued at any time due to severe unacceptable side effects, dose-limiting toxicities as defined, patient non-compliance with the defined treatment plan, if a patient becomes pregnant, requests to withdraw consent, or if the study doctor feels it is appropriate to do so.

Patients are withdrawn from study for disease progression, which can be defined by: 1) physical examination or radiographic evidence of disease recurrence, or 2) CA-125 elevation to twice the upper limits of normal (i.e. ≥70 U/ml), confirmed by a second sample also ≥70 U/ml. Time to treatment failure for biochemical relapse is recorded as the date of the first sample ≥70 U/ml.

Biostatistics

This is a phase I study designed to assess the safety and immunogenicity of a unimolecular pentavalent carbohydrate-based vaccine bearing Globo-H, GM2, sTn, TF and Tn on a single polypeptide backbone, conjugated to KLH, and mixed with the immunological adjuvant QS-21. It induces an IgG and IgM antibody response against these individual antigens and tumor cells expressing these antigens. Six patients are accrued to one of three pentavalent vaccine doses (25 mcg, 50 mcg and 10 or 100 mcg), and an expansion cohort of six patients are enrolled at the lowest immunogenic dose level where safety is met. Six patients are accrued per dose level in order to further evaluate safety and immune response at each dose level separately. Approximately 24 patients are accrued to this trial. The third dose level (10 or 100 mcg) is selected and prepared based on the serologic responses to the first two dose levels.

Progression to the next cohort will be based on no more than one DLT observed at a given cohort. If ≤1 DLT is observed, then escalation to the next dose occurs. If two patients experience a DLT, then the previous dose level is considered safe and further considered for immune response. For example, if 2 or more DLTs are seen at the 25 mcg level, the protocol de-escalates to 10 mcg.

A primary endpoint of this trial is to evaluate immunological response (IR) to the multiple antigen vaccine. A patient is considered a responder if he/she exhibits a serologic response to at least three of the five antigens of the vaccine at any of the follow-up time points up to week 23. A serologic response per component is defined as 1) an antibody titer of ≥1:80 by ELISA for patients with no detectable baseline titer, and 2) an antibody titer ≥8-fold increase over baseline by ELISA for patients with a detectable baseline titer. The proportion of responders will be estimated for each dose level.

The maximum number of responses is 30 (6 patients times 5 antigens). If both dose levels, 25 and 50 mcg, are deemed safe and if a difference of no more than 5 responses among 30 possible outcomes of the two consecutive dose levels is observed and at least 5/6 patients respond at 25 mcg, then de-escalation to dose level 10 mcg occurs. Otherwise, if the difference between adjacent dose levels is greater than 5/30 or 4 or fewer patients respond, then the next cohort is enrolled at 100 mcg. Among two consecutive dose levels where the difference in IR is less than or equal to 5/30 and both dose levels have at least 5 out of 6 patients respond then the lowest dose is defined as the lowest immunogenic dose level.

Twelve patients are accrued at the lowest immunogenic dose level and if at least 7 out of 12 patients are responders for three or more antigens based on the immune response criteria then the study is considered positive. This calculation assumes that the probability of immune response under the null hypothesis (i.e. no activity) is 0.35 versus the alternative hypothesis (i.e. target response probability) probability of 0.75. Type I error is set at 8% and Type II errors is set at 5%, using a single stage binomial proportion test. If less than 7 patients have an IR, the study concludes that the IR rate in this population is no better than 35%. (Yao T J, Begg C B, Livingston P, Optimal sample size for a series of pilot trials of new agents. Biometrics, 52(3): 992-1001, 1996.)

Progression free survival is defined from the first vaccination to disease progression or death. Kaplan-Meier methodology will be used to estimate PFS. DLT is determined up to week 7 (ie $4_{th}$ vaccination) and if <1 DLT is observed at week 7 in 1 of 6 enrolled patients, the next cohort can be enrolled.

The invention claimed is:
1. A method of treating ovarian cancer in a human subject suffering therefrom comprising administering to the subject a therapeutically effective amount of an immunogenic glycoconjugate having the structure of:

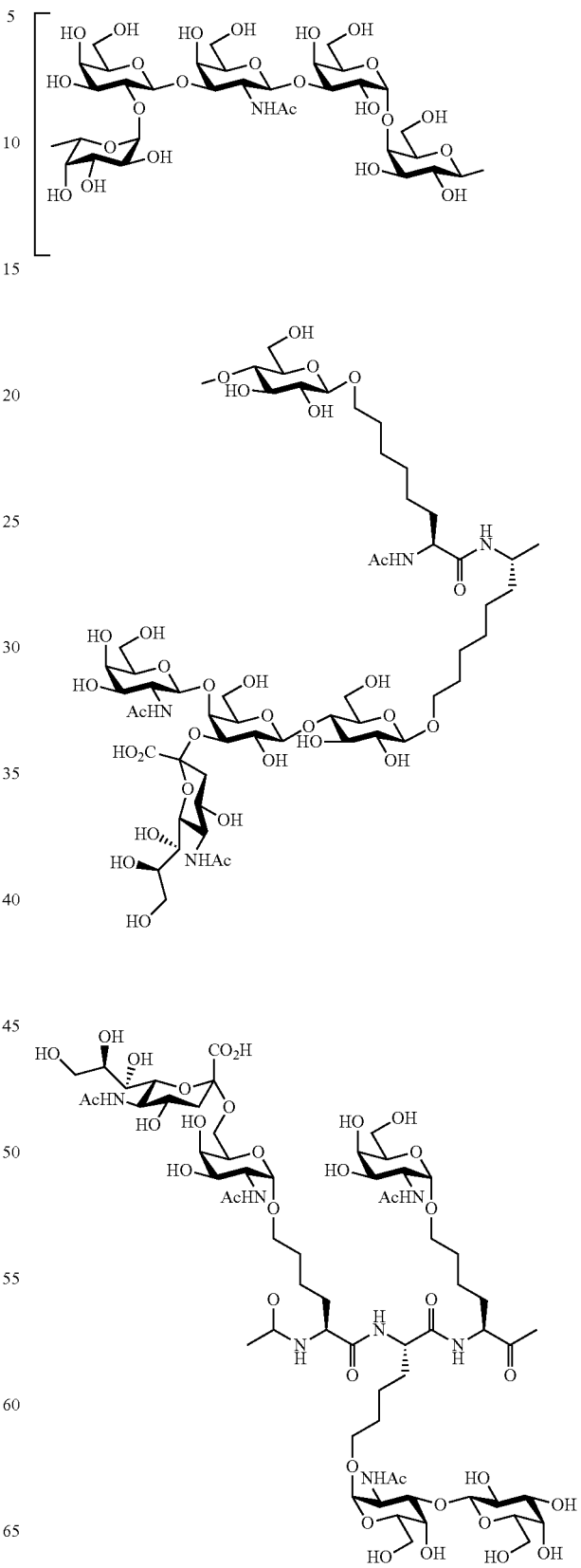

-continued

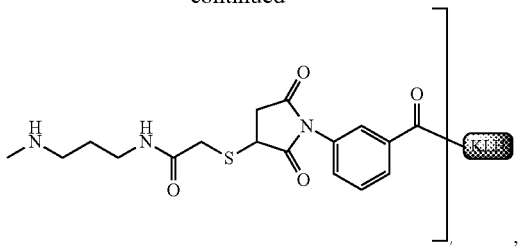

wherein t is the number of glycopeptide groups attached to the immunogenic carrier.

2. The method of claim 1, wherein the therapeutically effective amount comprises an amount effective to inhibit tumor growth.

3. The method of claim 1, wherein the therapeutically effective amount comprises an amount effective to elicit antibodies that recognize each of the carbohydrate antigens.

4. The method of claim 1, wherein the subject is in clinical remission, or where the subject has been treated by surgery and has limited unresected disease.

5. The method of claim 1, wherein the method further comprises co-administering one or more immunological adjuvants.

6. The method of claim 5, wherein at least one of said one or more immunological adjuvants is a saponin adjuvant, bacteria, liposomes, *Salmonella minnesota* cells, or bacille Calmette-Guerin.

7. The method of claim 1, wherein the method further comprises co-administering a pharmaceutically suitable carrier.

8. The method of claim 1, wherein t is from 50 to 1200.

9. The method of claim 1, wherein t is at least 200.

10. The method of claim 1, wherein t is at least 300.

11. The method of claim 1, wherein t is at least 500.

12. The method of claim 1, wherein t is from 200 to 800.

13. The method of claim 1, wherein t is from 300 to 800.

14. The method of claim 1, wherein t is from 500 to 800.

15. The method of claim 5, wherein at least one of said one or more immunological adjuvants is a saponin adjuvant.

16. The method of claim 5, wherein the immunological adjuvant is QS-21.

* * * * *